US009566221B2

(12) United States Patent
Degeorge et al.

(10) Patent No.: US 9,566,221 B2
(45) Date of Patent: Feb. 14, 2017

(54) METHODS FOR ALTERING THE COLOR AND APPEARANCE OF HAIR

(71) Applicant: L'OREAL, Paris (FR)

(72) Inventors: Michael Degeorge, Old Bridge, NJ (US); Frederic Legrand, Sevres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/441,529

(22) PCT Filed: Nov. 8, 2013

(86) PCT No.: PCT/US2013/069159
§ 371 (c)(1),
(2) Date: May 8, 2015

(87) PCT Pub. No.: WO2014/074825
PCT Pub. Date: May 15, 2014

(65) Prior Publication Data
US 2015/0265513 A1 Sep. 24, 2015

Related U.S. Application Data

(60) Provisional application No. 61/724,896, filed on Nov. 9, 2012.

(51) Int. Cl.
A61Q 5/10 (2006.01)
A61K 8/41 (2006.01)
A61Q 5/04 (2006.01)
A61Q 5/06 (2006.01)
A61K 8/02 (2006.01)

(52) U.S. Cl.
CPC ............ A61K 8/418 (2013.01); A61K 8/0204 (2013.01); A61Q 5/04 (2013.01); A61Q 5/06 (2013.01); A61Q 5/065 (2013.01); A61Q 5/10 (2013.01); A61K 2800/4324 (2013.01); A61K 2800/884 (2013.01)

(58) Field of Classification Search
CPC .............. A61Q 5/04; A61Q 5/05; A61Q 5/06; A61Q 5/065; A61Q 5/10; A61K 8/418; A61K 2800/4324; A61K 2800/884; A61K 2800/0204
USPC ..................................... 8/405; 132/202, 208
See application file for complete search history.

(56) References Cited

U.S. PATENT DOCUMENTS

| | | |
|---|---|---|
| 3,715,184 A | 2/1973 | Kuhling et al. |
| 3,775,332 A | 11/1973 | Heins et al. |
| 3,825,543 A | 7/1974 | Kuhling et al. |
| 3,869,454 A | 3/1975 | Lang et al. |
| 3,955,918 A | 5/1976 | Lang |
| 3,985,499 A | 10/1976 | Lang et al. |
| 4,003,699 A | 1/1977 | Rose et al. |
| 4,025,301 A | 5/1977 | Lang |
| 4,151,162 A | 4/1979 | Bugaut et al. |
| RE30,199 E | 1/1980 | Rose et al. |
| 4,540,510 A | 9/1985 | Karl |
| 5,061,289 A | 10/1991 | Clausen et al. |
| 5,293,885 A | 3/1994 | Darkwa et al. |
| 5,380,340 A | 1/1995 | Neunhoeffer et al. |
| 5,534,267 A | 7/1996 | Neunhoeffer et al. |
| 5,560,750 A | 10/1996 | Crews et al. |
| 5,618,523 A | 4/1997 | Zysman et al. |
| 5,663,366 A | 9/1997 | Neunhoeffer et al. |
| 5,708,151 A | 1/1998 | Mockli |
| 5,766,576 A | 6/1998 | Loewe et al. |
| 5,773,611 A | 6/1998 | Zysman et al. |
| 6,071,504 A | 6/2000 | Kawai et al. |
| 6,099,592 A | 8/2000 | Vidal et al. |
| 6,099,593 A | 8/2000 | Terranova et al. |
| 6,284,003 B1 | 9/2001 | Rose et al. |
| 6,338,741 B1 | 1/2002 | Vidal et al. |
| 6,645,258 B2 | 11/2003 | Vidal et al. |
| 6,846,333 B2 | 1/2005 | Legrand et al. |
| 6,953,584 B1 | 10/2005 | Samain et al. |
| 7,066,966 B2 | 6/2006 | Cottard et al. |
| 7,172,633 B2 | 2/2007 | Samain et al. |
| 7,220,286 B2 | 5/2007 | Greaves |
| 7,244,420 B1 | 7/2007 | Samain et al. |
| 7,250,064 B2 | 7/2007 | Plos et al. |
| 7,311,736 B2 | 12/2007 | Burgaud et al. |
| 7,399,320 B2 | 7/2008 | Burgaud et al. |
| 7,495,037 B2 | 2/2009 | Moszner et al. |
| 7,566,348 B2 | 7/2009 | Narasimhan et al. |
| 7,582,122 B2 | 9/2009 | Daubresse et al. |

(Continued)

FOREIGN PATENT DOCUMENTS

| | | | |
|---|---|---|---|
| DE | 2359399 A1 | 6/1975 | |
| DE | 3843892 A1 | 6/1990 | |

(Continued)

OTHER PUBLICATIONS

Todd, Charles, et al., "Volatile Silicone Fluids for Cosmetic Formulations," Cosmetics and Toiletries, vol. 91, pp. 29-32, Jan. 1976.
International Search Report and Written Opinion for Application No. PCT/US2013/069136, mailed Mar. 5, 2014, 3 pages.
International Search Report and Written Opinion for Application No. PCT/US2013/069159, mailed Mar. 18, 2014, 3 pages.
Wertz et al., "Essential Fatty Acids and Epidermal Integrity," Downing in Arch, Dermatol, vol. 123, 1987, pp. 1381-1384.
William M. Meylan and Philip H. Howard, "Atom/Fragment Contribution Method for Estimating Octanol-Water Partition Coefficients," Journal of Pharmaceutical Sciences, vol. 84, No. 1: pp. 83-92, 1995.
English language Abstract for DE 102006031470A1 (Sep. 6, 2007).
English language Abstract for DE 102010043497A1 (Sep. 22, 2011).
English language Abstract for FR 2633940A1 (Jan. 12, 1990).
English language Abstract for FR 2789896A1 (Aug. 25, 2000).
English language Abstract for JPH02-19576A (Jan. 23, 1990).

(Continued)

Primary Examiner — Eisa Elhilo
(74) Attorney, Agent, or Firm — The Marbury Law Group, PLLC

(57) ABSTRACT

Disclosed are methods and compositions for altering the color of hair, comprising treating the hair with a pre-alkalizing composition and then treating the hair with a color-altering composition comprising at least one direct dye and optionally at least one oxidative dye precursor.

20 Claims, No Drawings

(56) References Cited

U.S. PATENT DOCUMENTS

| | | | |
|---|---|---|---|
| 7,662,193 | B2 | 2/2010 | Matsunaga et al. |
| 7,771,492 | B2 | 8/2010 | Cottard et al. |
| 7,806,939 | B2 | 10/2010 | Cohen et al. |
| 8,323,356 | B2 | 12/2012 | Gross et al. |
| 8,328,879 | B2 | 12/2012 | Gross et al. |
| 8,556,992 | B2 | 10/2013 | DeGeorge et al. |
| 2002/0050013 | A1 | 5/2002 | Vidal et al. |
| 2003/0019051 | A9 | 1/2003 | Vidal et al. |
| 2003/0084517 | A1 | 5/2003 | Tsujino et al. |
| 2003/0099605 | A1 | 5/2003 | Browning |
| 2003/0169221 | A1 | 9/2003 | Stephenson et al. |
| 2004/0194231 | A1 | 10/2004 | Guerin et al. |
| 2004/0205905 | A1 | 10/2004 | Plos |
| 2004/0209019 | A1 | 10/2004 | Demars et al. |
| 2005/0028300 | A1 | 2/2005 | Burgaud et al. |
| 2005/0071933 | A1 | 4/2005 | Rondeau |
| 2005/0076459 | A1 | 4/2005 | Guardia, Jr. et al. |
| 2005/0165129 | A1 | 7/2005 | Moszner et al. |
| 2005/0191251 | A1 | 9/2005 | Kravtchenko et al. |
| 2006/0054823 | A1 | 3/2006 | Yon et al. |
| 2006/0064823 | A1 | 3/2006 | Marsh et al. |
| 2006/0117496 | A1 | 6/2006 | Bolton et al. |
| 2006/0156479 | A1 | 7/2006 | Hercouet et al. |
| 2007/0169286 | A1 | 7/2007 | Narasimhan et al. |
| 2008/0092307 | A1 | 4/2008 | Burgaud et al. |
| 2008/0184495 | A1 | 8/2008 | Brun et al. |
| 2008/0223392 | A1 | 9/2008 | Cannell et al. |
| 2009/0071494 | A1 | 3/2009 | Nguyen et al. |
| 2009/0265866 | A1 | 10/2009 | Eliu et al. |
| 2009/0282623 | A1 | 11/2009 | Goget et al. |
| 2010/0083446 | A1 | 4/2010 | Brun et al. |
| 2010/0126522 | A1 | 5/2010 | Fujinuma et al. |
| 2010/0179105 | A1 | 7/2010 | Blin et al. |
| 2010/0192969 | A1 | 8/2010 | Degeorge et al. |
| 2011/0047712 | A1 | 3/2011 | Gross et al. |
| 2011/0088711 | A1 | 4/2011 | Bonafos |
| 2011/0146005 | A1 | 6/2011 | Gross et al. |
| 2011/0146006 | A1 | 6/2011 | Gross et al. |
| 2011/0146007 | A1 | 6/2011 | Goget et al. |
| 2011/0182839 | A1 | 7/2011 | Numata |
| 2011/0200543 | A1 | 8/2011 | Josso |
| 2011/0232669 | A1 | 9/2011 | Suenger et al. |
| 2012/0227756 | A1 | 9/2012 | Gross et al. |
| 2012/0246841 | A1 | 10/2012 | Gross et al. |
| 2013/0167862 | A1 | 7/2013 | Lopez et al. |
| 2014/0305464 | A1 | 10/2014 | DeGeorge et al. |
| 2014/0311517 | A1 | 10/2014 | DeGeorge et al. |
| 2014/0326270 | A1 | 11/2014 | DeGeorge et al. |
| 2015/0290093 | A1 | 10/2015 | Salvemini et al. |

FOREIGN PATENT DOCUMENTS

| | | | | |
|---|---|---|---|---|
| DE | 4133957 | A1 | 4/1993 | |
| DE | 19543988 | A1 | 5/1997 | |
| DE | 102006031470 | A1 | 9/2007 | |
| DE | 102010043497 | A1 | 9/2011 | |
| EP | 0714954 | A2 | 6/1996 | |
| EP | 1378544 | A2 | 1/2004 | |
| EP | 1510197 | A1 | 3/2005 | |
| EP | 1674073 | A1 | 6/2006 | |
| EP | 1970099 | A2 | 9/2008 | |
| EP | 2020254 | A1 | 2/2009 | |
| EP | 2338470 | A1 | 6/2011 | |
| FR | 2140205 | A1 | 1/1973 | |
| FR | 2189006 | A1 | 1/1974 | |
| FR | 2285851 | A1 | 4/1976 | |
| FR | 2633940 | A1 | 1/1990 | |
| FR | 2673179 | A1 | 8/1992 | |
| FR | 2733749 | A1 | 11/1996 | |
| FR | 2750048 | A1 | 12/1997 | |
| FR | 2789896 | A1 | 8/2000 | |
| FR | 2820032 | A1 | 8/2002 | |
| FR | 2936413 | A1 | 4/2010 | |
| GB | 1026978 | A | 4/1966 | |
| GB | 1153196 | A | 5/1969 | |
| GB | 2219352 | A | 12/1989 | |
| JP | H0219576 | A | 1/1990 | |
| JP | H05155742 | A | 6/1993 | |
| JP | H09110659 | A | 4/1997 | |
| KR | 1019980077541 | A | 11/1998 | |
| KR | 1020090019132 | A | 2/2009 | |
| WO | 9408969 | A1 | 4/1994 | |
| WO | 9408970 | A1 | 4/1994 | |
| WO | 9501772 | A1 | 1/1995 | |
| WO | 9515144 | A1 | 6/1995 | |
| WO | 9615765 | A1 | 5/1996 | |
| WO | 0122931 | A1 | 4/2001 | |
| WO | 0122932 | A1 | 4/2001 | |
| WO | 0162221 | A1 | 8/2001 | |
| WO | WO 01/62221 | A1 * | 8/2001 | ............... A61K 7/13 |
| WO | 0179644 | A1 | 10/2001 | |
| WO | 2008136433 | A1 | 11/2008 | |
| WO | 2009/010883 | A2 | 1/2009 | |
| WO | 2010054981 | A2 | 5/2010 | |
| WO | 2010133658 | A2 | 11/2010 | |
| WO | 2011/009563 | A2 | 1/2011 | |
| WO | 2011056332 | A1 | 5/2011 | |
| WO | 2011/076358 | A1 | 6/2011 | |
| WO | 2011064007 | A1 | 6/2011 | |
| WO | 2011069786 | A2 | 6/2011 | |
| WO | 2011076792 | A1 | 6/2011 | |
| WO | 2011079974 | A2 | 7/2011 | |
| WO | 2011/131603 | A1 | 10/2011 | |
| WO | 2011137338 | A2 | 11/2011 | |
| WO | 2011139433 | A2 | 11/2011 | |
| WO | 2012049146 | A2 | 4/2012 | |
| WO | 2013/071191 | A1 | 5/2013 | |
| WO | 2013071182 | A1 | 5/2013 | |
| WO | 2013071192 | A1 | 5/2013 | |
| WO | 2013071194 | A1 | 5/2013 | |
| WO | 2014074812 | A1 | 5/2014 | |

OTHER PUBLICATIONS

English language Abstract for JPH05-155742A (Jun. 22, 1993).
English language Abstract for JPH09-110659A (Apr. 28, 1997).
K. Robson, M.E. Stewart, S. Michelsen, N.D. Lazo, D.T. Downing "6-Hydroxy-4-sphingenine in human epidermal ceramides"—Journal of Lipid Research, vol. 35, 1994, p. 2060-2068.
International Search Report and Written Opinion for PCT/US2012/064545 (Nov. 9, 2012).
International Search Report and Written Opinion for PCT/US2012/064555 (Nov. 9, 2012).
International Search Report and Written Opinion for PCT/US2012/064561 (Nov. 9, 2012).
International Preliminary Report on Patentability and Written Opinion for PCT/US2012/064545 (May 22, 2014).
International Preliminary Report on Patentability and Written Opinion for PCT/US2012/064557 (May 22, 2014).
International Preliminary Report on Patentability and Written Opinion for PCT/US2012/064559 (May 22, 2014).
International Preliminary Report on Patentability and Written Opinion for PCT/US2012/064555 (May 13, 2014).
International Preliminary Report on Patentability and Written Opinion for PCT/US2012/064561 (May 13, 2014).
Supplementary European Search Report for PCT/US2012/064557 (Jul. 14, 2015).
Supplementary European Search Report for PCT/US2012/064559 (Jul. 24, 2015).
Extended European Search Report for counterpart European Application No. 12848141 (Nov. 3, 2015).
Extended European Search Report for counterpart Application No. PCT/US2013/069136, mailed May 23, 2016.

* cited by examiner

METHODS FOR ALTERING THE COLOR AND APPEARANCE OF HAIR

CROSS-REFERENCE TO RELATED APPLICATIONS

This is a national stage application of PCT/US2013/069159, filed internationally on Nov. 8, 2013, which claims priority to U.S. Provisional Patent Application No. 61/724,896, filed Nov. 9, 2012, both of which are hereby incorporated by reference in their entireties.

BACKGROUND OF THE INVENTION

Chemical treatments on human hair, such as relaxers, straighteners, waves, perms, oxidative and direct dyes, highlights, lightening compositions and bleaches, are generally known to result in hair breakage and loss, dryness, roughness and brittleness, and skin and/or scalp irritation. Such chemical treatments employ various reducing and oxidizing agents, alkalizing agents, and coloring agents that help re-shape, artificially color, decolorize, modify the color shade/tone, or enhance the appearance and color of hair. Often times, these chemical treatments are used with the application of heat and mechanical combing or brushing, which may contribute to adversely affecting the condition of the hair and the hair cuticle.

Thus, conventional and customary practice by consumers and hair dressers is to have a waiting period of at least 24 hours, preferably two weeks, in between two different chemical hair treatments in order to prevent or reduce irritation to the skin or scalp and the potential damage to hair caused by different chemical treatments within a short period of time, e.g., a few hours.

One example of the problems encountered with successively chemically treating the hair is that such chemical treatments may prevent the hair's color or shade from being lightened, bleached, dyed or altered correctly after the chemical treatment, and therefore, prevent the consumer from achieving the desired lightening or shade/color effects, especially when the lightening, bleaching, coloration or color-altering step is conducted immediately after the chemical treatment. Thus, a waiting period of at least 24 hours is generally recommended in order to reduce the chance of having a reaction between the different chemical treatments, for example, straightening then bleaching the hair, that could potentially result in an undesirable hair color or shade.

In order to address the concerns mentioned above, methods and compositions have been proposed such as those that involve the use of alternative ingredients and/or ingredients and compositions that are less harsh on hair and skin, including hair treatment regimens that may minimize the problems arising from successive chemical treatments. However, there still exists a need to improve such methods and compositions in order to formulate color-altering products and hair treatment regimens or systems that allow the consumer to successively chemically treat hair in a convenient and efficient manner, which effectively alter the color of and/or re-shape the hair while minimizing the damage to the hair and other adverse effects to the consumer.

BRIEF SUMMARY OF THE INVENTION

The present disclosure is directed to methods and compositions for altering the appearance of hair. Exemplary methods comprise applying a pre-alkalizing composition to the hair, and subsequently applying a color-altering composition to the hair. In at least certain exemplary embodiments, the methods and compositions described allow for successive chemical treatments of the hair, while minimizing damage to the hair and/or skin (e.g. scalp).

By way of example, there is a need to provide methods and compositions that provide for hair to be chemically treated (e.g. straightened), and then subsequently colored or lightened, while achieving a desired change in hair tone and minimizing damage to the hair. Lightening of the hair is typically evaluated by the tone height or level which describes the degree or level of lightening. The notion of "tone" is based on the classification of the natural shades, one tone separating each shade from the shade immediately following or preceding it, which is well known to hairstyling professionals. The tone heights or color levels range from 1 (black) to 10 (light blond), one unit corresponding to one tone; thus, the higher the number, the lighter the shade.

Accordingly, in various exemplary embodiments of the disclosure, the methods and compositions described allow one to achieve a desired level of color or color "lift" in tone, i.e. to a higher number, while minimizing damage to the hair and/or skin. In further exemplary embodiments, the methods and compositions described below allow one to deposit color onto hair with no or minimal lift in the color.

Various exemplary methods according to the disclosure comprise:
   (a) applying onto the hair, a pre-alkalizing composition having a pH of from about 8 to about 14 to form pre-alkalized hair;
   (b) optionally, rinsing the hair;
   (c) applying a color-altering composition onto the pre-alkalized hair, wherein the color-altering composition comprises, in a cosmetically acceptable carrier,
     (i) at least one direct dye; and
     (ii) optionally at least one oxidative dye precursor;
       and wherein the pH of the color-altering composition ranges from about 1 to about 7;
   (d) leaving the color-altering composition on the hair for a time period sufficient to achieve a desired color; and
   (e) optionally, rinsing the hair;
wherein the color-altering composition does not comprise a chemical oxidizing agent; and
wherein the color-altering composition is applied onto the pre-alkalized hair within about 24 hours after the pre-alkalizing step.

Optionally, the color-altering composition additionally comprises at least one additional ingredient chosen from fatty substances, de-dusting agents, alkoxyaminosilicones, silane compounds, ceramide compounds, and metal catalyst compounds.

In further embodiments, methods for minimizing damage to the hair during a process for altering the color of the hair are disclosed. Compositions useful for altering the appearance of the hair, and for minimizing damage to the hair, are also disclosed.

It is to be understood that both the foregoing general description and the following detailed description are exemplary and explanatory only, and are not restrictive of the invention as claimed. Other embodiments will be apparent to those skilled in the art from consideration of the specification and practice of the embodiments disclosed herein. It is intended that the specification and examples be considered as exemplary only, with the true scope and spirit of the invention being indicated by the claims.

It is also to be understood that, while in various embodiments described herein, steps of exemplary methods are recited in a particular order, it is intended that the disclosed steps may be carried out in any order such that the properties intrinsically associated with the methods are not, or are not substantially, adversely affected.

DETAILED DESCRIPTION

Exemplary embodiments of the disclosure comprise applying a pre-alkalizing composition to the hair, and subsequently applying a color-altering composition to the hair.

Pre-Alkalizing Composition

Various embodiments of the present invention provide for applying a pre-alkalizing composition to the hair in a first step of the methods described herein. By first applying a pre-alkalizing composition to the hair, the hair is in a pre-alkalized form prior to further chemical treatments. Without wishing to be bound by theory, it is believed that the pre-alkalizing step opens the hair cuticle, thereby rendering it more susceptible to penetration by the subsequently-applied composition. This in turn is believed to render the hair coloring, straightening, relaxing, etc., process more efficient and less time-consuming, while minimizing damage.

The pre-alkalizing step may, for example, use an alkaline composition having a pH ranging from about 8 to about 14, such as about 8 to about 10.5, or about 8.5 to about 9.5. Acceptable alkaline compositions useful herein are known in the art. By way of example, any conventional base, whether alkaline hydroxide or non-hydroxide, may be chosen as the pre-alkalizing composition, so long as it results in the formation of a pre-alkalizing composition having the above-disclosed pH range. The precise amount of conventional base used will depend on the specific base or bases chosen, which can be determined through routine experimentation by those of ordinary skill in the art. The pre-alkalizing composition may further comprise a cosmetically acceptable carrier.

The pre-alkalizing composition may be employed in any suitable form, so long as the hair, after application of the pre-alkalizing composition, has a pH that is alkaline. Examples include, but are not limited to, an alkaline shampoo, an alkaline conditioner, or an alkaline solution in general. In further exemplary embodiments, the pre-alkalizing composition may be a chemical treatment composition that is alkaline and that causes a chemical reaction on the hair, such as, for example, relaxing, straightening, waving, perming, lightening the color, and/or permanent, semi-permanent or demi-permanent coloring of the hair. In one exemplary embodiment, the pre-alkalizing composition is in the form of an alkaline shampoo which would facilitate both the pre-alkalizing and cleaning of the hair at the same time.

In various exemplary embodiments, the pre-alkalizing composition may optionally comprise at least one auxiliary ingredient. Exemplary auxiliary ingredients useful in the pre-alkalizing composition according to various embodiments of the disclosure include, but are not limited to, surfactants, rheology-modifying agents, chelants, fatty substances, ceramides, substantive polymers (cationic and/or amphoteric), an anhydrous and/or inert liquid, alkoxyaminosilicones, and silanes, as well as other components typically used in cosmetic compositions, such as, for example, fragrances.

The pre-alkalizing composition may be applied to the hair and remain in contact with the hair for a period of time sufficient to form pre-alkalized hair. For example, the pre-alkalizing composition may be left on the hair for up to one hour, such as from about 5 minutes to about 50 minutes, from about 10 minutes to about 40 minutes, or from about 15 minutes to about 30 minutes. In various exemplary embodiments, the pre-alkalizing composition may be left on the hair for up to about 20 minutes, such as up to about 15 minutes, or up to about 10 minutes.

Once the hair has been pre-alkalized, the pre-alkalizing composition may, optionally, be rinsed off the hair before further chemical treatment is applied.

In various exemplary embodiments, after the hair has been pre-alkalized, and optionally the pre-alkalizing composition rinsed, the hair may optionally be shampooed and rinsed before further chemical treatment is applied.

Color-Altering Composition

As a second step in various embodiments according to the disclosure, a color-altering composition may be applied to the pre-alkalized hair. The color-altering composition may, in at least certain embodiments, be in a ready-to-use form.

The color-altering composition may, in various embodiments, be applied onto the hair within about 24 hours, such as less than 24 hours or less than 12 hours, after the pre-alkalizing step. In at least certain exemplary embodiments, the color-altering composition may be applied to the hair within a few hours (e.g. about 1 to about 6 hours) or a few minutes (e.g. up to about 60 minutes) after the pre-alkalizing step.

According to various embodiments, the color-altering composition comprises, in a cosmetically acceptable carrier, at least one direct dye.

As examples of synthetic direct dyes that are suitable for use, mention may be made of azo direct dyes, methine direct dyes, carbonyl direct dyes, azine direct dyes, nitro (hetero) aryl direct dyes, especially nitrobenzene dyes, and tri(hetero)arylmethane direct dyes, and the addition salts thereof; alone or as mixtures.

For example, the azo dyes may comprise an —N=N— function in which the two nitrogen atoms are not simultaneously engaged in a ring. However, it is not excluded for one of the two nitrogen atoms of the sequence —N=N— to be engaged in a ring.

The dyes of the methine family are, by way of example, compounds comprising at least one sequence chosen from >C=C< and —N=C< in which the two atoms are not simultaneously engaged in a ring. However, it is pointed out that one of the nitrogen or carbon atoms of the sequences may be engaged in a ring. More particularly, the dyes of this family are derived from compounds of true methine type (comprising one or more abovementioned sequences —C=C—); of azomethine type (comprising at least one, or more, sequences —C=N—) with, for example, azacarbocyanins and their isomers, diazacarbocyanins and their isomers, and tetraazacarbocyanins; of mono- and diarylmethane type; of indoamine (or diphenylamine) type; of indophenol type; or of indoaniline type.

As regards the dyes of the carbonyl family, examples that may be mentioned include dyes chosen from acridone, benzoquinone, anthraquinone, naphthoquinone, benzanthrone, anthranthrone, pyranthrone, pyrazol-anthrone, pyrimidinoanthrone, flavanthrone, idanthrone, flavone, (iso)violanthrone, isoindolinone, benzimid-azolone, isoquinolinone, anthrapyridone, pyrazolo-quinazolone, perinone, quinacridone, quinophthalone, indigoid, thioindigo, naphthalimide, anthrapyrimidine, diketopyrrolopyrrole and coumarin dyes.

As regards the dyes of the azine family, mention may be made, for example, of azine, xanthene, thioxanthene, fluorindine, acridine, (di)oxazine, (di)thiazine and pyronin dyes.

The nitro (hetero) aromatic dyes are more particularly nitrobenzene or nitropyridine direct dyes.

As regards the dyes of porphyrin or phthalocyanin type, it is possible to use cationic or non-cationic compounds, optionally comprising one or more metals or metal ions, for instance alkali metals, alkaline-earth metals, zinc and silicon. Examples of particularly suitable synthetic direct dyes that may be mentioned include nitrobenzene dyes; azo direct dyes; methine direct dyes; azomethine direct dyes, with, more particularly, diazacarbocyanins and isomers thereof and tetraazacarbocyanins (tetraazapentamethines); quinone direct dyes, and in particular anthraquinone, naphthoquinone or benzoquinone dyes; azine direct dyes; xanthene direct dyes; triarylmethane direct dyes; indoamine direct dyes; indigoid direct dyes; phthalocyanin and porphyrin direct dyes; alone or as mixtures.

The direct dyes may be chosen from nitrobenzene dyes; azo dyes; azomethine dyes, with diazacarbocyanins and isomers thereof, and tetraazacarbocyanins (tetraazapentamethines); anthraquinone direct dyes; triarylmethane direct dyes; alone or as mixtures.

For example, these direct dyes may be chosen from nitrobenzene direct dyes; azo direct dyes; azomethine direct dyes, with diazacarbocyanins and isomers thereof, and tetraazacarbocyanins (tetraaza pentamethines); alone or as a mixture.

Among the nitrobenzene direct dyes that may be used, mention may be made in a non-limiting manner of the following compounds: 1,4-diamino-2-nitrobenzene; I-amino-2-nitro-4-hydroxyethylaminobenzene; I-amino-2-nitro-4-bis(beta-hydroxyethyl)aminobenzene; 1,4-bis(beta-hydroxyethylamino)-2-nitrobenzene; I-hydroxyethylamino-2-nitro-4-bis(beta-hydroxy-ethylamino)benzene; 1-beta-hydroxyethyl amino-2-nitro-4-aminobenzene; I-hydroxyethylamino-2-nitro-4-(ethyl) (beta-hydroxy-ethyl) aminobenzene; I-amino-3-methyl-4-hydroxyethylamino-6-nitro-benzene; I-amino-2-nitro-4-hydroxyethylamino-5-chloro-benzene; 1,2-diamino-4-nitrobenzene; I-amino-2-hydroxyethylamino-5-nitrobenzene; 1,2-bis(beta-hydroxyethylamino)-4-nitrobenzene; I-amino-2-tris (hydroxymethyl)methyl-amino-5-nitro-benzene; I-hydroxy-2-amino-5-nitrobenzene; 1-hydroxy-2-amino-4-nitrobenzene; I-hydroxy-3-nitro-4-aminobenzene; I-hydroxy-2-amino-4,6-dinitrobenzene; I-hydroxyethyloxy-2-hydroxyethylamino-5-nitro-benzene; 1-ethoxy-2-hydroxyethylamino-5-nitrobenzene; I-hydroxyethyloxy-3-methylamino-4-nitrobenzene; 1-beta, α-dihydroxypropyloxy-3-methylamino-4-nitro benzene; 1-hydroxyethylamino-4, Y-dihydroxypropyloxy-2-nitrobenzene; 1-beta, Y-dihydroxypropylamino-4-trifluoromethyl-2-nitrobenzene; 1-beta-hydroxyethylamino-4-trifluoromethyl-2-nitro-benzene; 1-beta-hydroxyethylamino-3-methyl-2-nitrobenzene; 1-beta-aminoethylamino-5-methoxy-2-nitrobenzene; 1-hydroxy-2-chloro-6-ethylamino-4-nitrobenzene; 1-hydroxy-2-chloro-6-amino-4-nitrobenzene; 1-hydroxy-6-bis(beta-hydroxyethyl)amino-3-nitro-benzene; α-beta-hydroxyethylamino-2-nitrobenzene; and I-hydroxy-4-beta-hydroxyethylamino-3-nitrobenzene.

Among the azo, azomethine, and methine direct dyes that may be used according to the invention, mention may be made of the cationic dyes described in patent applications WO 95/15144, WO 95/01772 and EP714954; FR2189006, FR2285851, FR2140205, EP1378544 and EP1674073, all of which are incorporated by reference herein.

For example, the synthetic direct dyes may be chosen from monochromophoric cationic direct dyes of the following types: azos; methines; azomethines with diazacarbocyanins and isomers thereof, and tetraazacarbocyanins; anthraquinones; alone or as a mixture.

Hence, mention may be made especially of the cationic direct dyes corresponding to the following formula (XVIII):

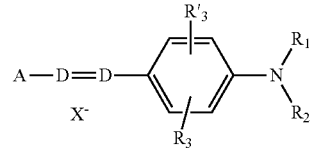

wherein, in formula (XVIII):
D represents a nitrogen atom or the —CH group,
R₁ and R₂, which may be identical or different, represent a hydrogen atom; a $C_1$-C4 alkyl radical which may be substituted with a —CN, —OH or —NH₂ radical, or form, with a carbon atom of the benzene ring, an optionally oxygenous or nitrogenous heterocycle that may be substituted with one or more $C_1$-$C_4$ alkyl radicals; a 4'-aminophenyl radical,
R₃ and R'₃, which are identical or different, represent a hydrogen or halogen atom chosen from chlorine, bromine, iodine and fluorine, or a cyano, $C_1$-$C_4$ alkyl, $C_1$-C4 alkoxy or acetyloxy radical,
X⁻ represents an anion chosen from chloride, methyl sulfate and acetate,
A represents a group chosen from the following structures:

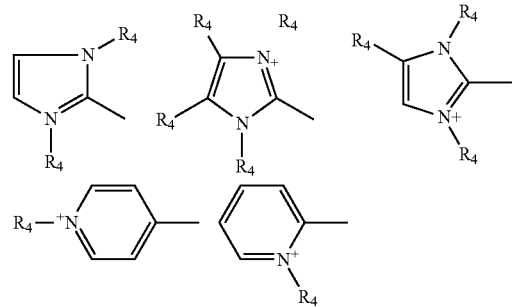

in which R₄ represents a $C_1$-$C_4$ alkyl radical that may be substituted with a hydroxyl radical;

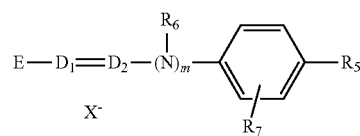

wherein:
R₅ represents a hydrogen atom, a $C_1$-$C_4$ alkoxy radical or a halogen atom such as bromine, chlorine, iodine or fluorine, R₆ represents a hydrogen atom or a $C_1$-$C_4$ alkyl radical or forms, with a carbon atom of the benzene ring, a heterocycle that is optionally oxygenous and/or substituted with one or more $C_1$-$C_4$ alkyl groups,
R₇ represents a hydrogen or halogen atom such as bromine, chlorine, iodine or fluorine, $D_1$ and $D_2$ independently represent a nitrogen atom or the —CH group, m=0 or 1, $X^-$ represents a cosmetically acceptable anion that is chosen from chloride, iodide, methyl sulfate, ethyl sulfate and acetate, E represents a group chosen from the following structures:

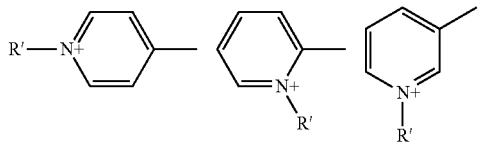

wherein:

R' represents a $C_1$-$C_4$ alkyl radical; and when m=0 and when $D_1$ represents a nitrogen atom, E may then also denote a group of the following structure:

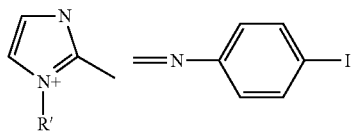

As other dyes that may be used according to the invention, mention may also be made, among the azo direct dyes, of the following dyes, which are described in the Colour Index International, 3rd edition, incorporated by reference herein: Disperse Red 17; Disperse Red 13; Basic Red 22; Basic Red 76; Basic Yellow 57; Basic Brown 16; Basic Brown 17; Disperse Green 9; Disperse Black 9; Solvent Black 3; Disperse Blue 148; Disperse Violet 63; and Solvent Orange 7. Other azo dyes that may be used according to the invention include Basic Red 46, Basic Violet 35, and Disperse Orange 3.

Mention may also be made of I-(4'-aminodiphenylazo)-2-methyl-4-bis(beta-hydroxyethyl)amino-benzene (INCI name: HC Yellow 7).

Among the quinone direct dyes that may be mentioned are the following dyes: Disperse Red 15; Solvent Violet 13; Solvent Blue 14; Disperse Violet 1; Disperse Violet 4; Disperse Blue 1; Disperse Violet 8; Disperse Blue 3; Disperse Red 11; Disperse Blue 7; Disperse Blue 14; Basic Blue 22; Disperse Violet 15; Disperse Blue 377; Disperse Blue 60; Basic Blue 99; and also the following compounds: I-N-methylmorpholiniumpropylamino-4-hydroxyanthraquinone; I-aminopropylamino-4-methylaminoanthraquinone; 1-aminopropylamino-anthraquinone; 5-beta-hydroxyethyl-1,4-diaminoanthraquinone; 2-aminoethylaminoanthraquinone; and 1,4-bis(beta-dihydroxypropylamino) anthraquinone.

Mention may also be made of the coumarin compound Disperse Yellow 82.

Among the azine dyes that may be mentioned are the following compounds: Basic Blue 17; Basic Red 2; Solvent Orange 15.

Among the triarylmethane dyes that may be used according to the invention, mention may be made of the following compounds: Basic Green 1; Basic Violet 3; Basic Violet 14; Basic Blue 7; Basic Blue 26.

Among the indoamine dyes that may be used according to the invention, mention may be made of the following compounds: 2-hydroxyethylamino-5-[bis(beta-4'-hydroxyethyl)amino]anilino-1,4-benzoquinone; 2-hydroxyethylamino-5-(2'-methoxy-4'-amino)anilino-1,4-benzoquinone; 3-N(2'-chloro-4'-hydroxy)phenylacetylamino-6-methoxy-1,4-benzoquinone imine; 3-N(3'-chloro-4'-methylamino)phenylureido-6-methyl-1,4-benzoquinone imine; 3-[4'-N-(ethylcarbamylmethyl)amino]phenylureido-6-methyl-1,4-benzoquinone imine.

The cationic direct dyes may be, for example, chosen from direct dyes of the following types: azos, methines; azomethines, with diazacarbocyanins and isomers thereof, and tetraazacarbocyanins (tetraazapentamethines); anthraquinones; alone or as a mixture.

For the nonionic dyes, compounds with a log P of greater than or equal to 2 may be chosen. As regards the synthetic direct dyes with a log P of greater than or equal to 2, it is known that the log P value conventionally represents the partition coefficient of the dye between octanol and water. The log P may be calculated according to the method described in the article by Meylan and Howard: Atom/Fragment contribution method for estimating octanol-water partition coefficients, J. Pharm. Sci., 84: 83-92, 1995, incorporated by reference herein. This value may also be calculated using numerous commercially available software packages, which determine the log P as a function of the structure of a molecule. By way of example, mention may be made of the Epiwin software from the United States Environmental Agency.

For example, the dyes that are suitable for use in the invention are chosen from the following compounds, alone or as a mixture:

Dye Chemical structure logP

Disperse Red 17 3.69

Disperse Violet 1 3.0

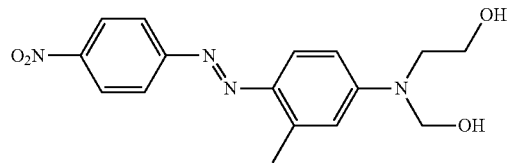

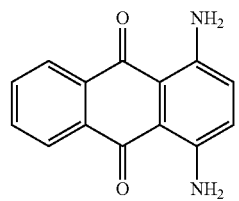

HC Yellow 7 2.38

Disperse Blue 377 3.21

Disperse Red 13 5.22

Disperse Green 9 4.23

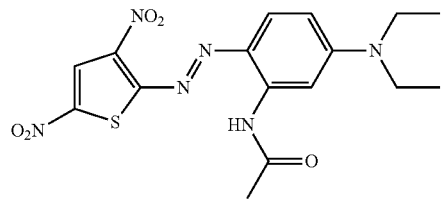 [SMILES: CCN(CC)c1ccc(/N=N/c2sc([N+](=O)[O-])cc2[N+](=O)[O-])c(NC(C)=O)c1]

Solvent Black 3$^N$ VJTV 7.50
Disperse Blue 148 4.81
Disperse Violet 63 5.30
Disperse Blue 60 3.38

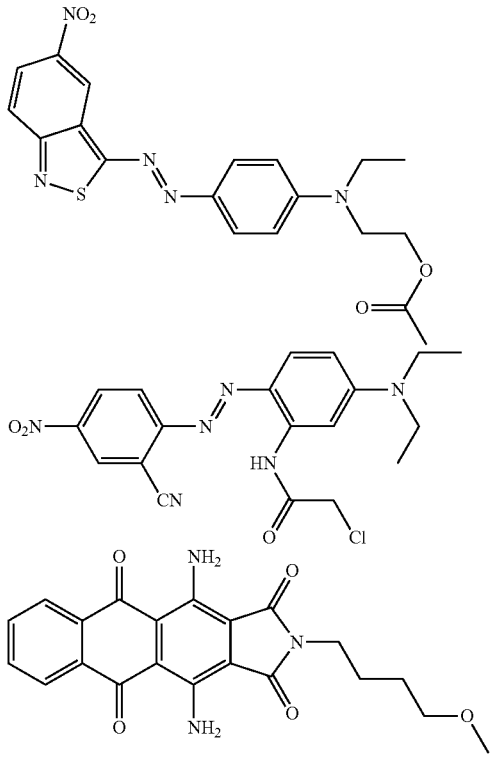

OHN""
Disperse Blue 14 4.25
OHN
Solvent Orange 15 3.90
Solvent Orange 7 4.40 O N—
Solvent Blue 14 8.18
OHN—
Disperse Yellow 82 3.68

For example, the direct dyes of the invention are chosen from cationic dyes of the following types: azos; methines; azomethines, with diazacarbocyanins and isomers thereof, and tetraaza-carbocyanins (tetraazapentamethines); anthraquinones; alone or as a mixture, and in particular dyes (AI) to (A6) mentioned previously, and also nonionic dyes with a log P of greater than or equal to 2.

Among the anionic direct dyes, mention may be made in particular of those described in the Colour Index International 3rd edition under the name Acid, and in particular: Disperse Red 17; Acid Yellow 9; Acid Black 1; Acid Yellow 36; Acid Orange 7; Acid Red 33; Acid Red 35; Acid Yellow 23; Acid Orange 24; Acid Violet 43; Acid Blue 62; Acid Blue 9; Acid Violet 49; and Acid Blue 7.

Exemplary direct dyes that may be used include those that are nonionic, anionic, and cationic. For example, the direct dye may be chosen from nitrobenzene dyes, and acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanin (such as in particular azacarbocyanin, diazacarbocyanin, diazahemicyanin, hemicyanin, tetraazacarbocyanin), diazine, diketopyrrolopyrrole, dioxazine, diphenylamine, diphenylmethane, dithiazine, flavanthrone, flavone, fluorindine, formazan, hydrazone, hydroxy ketone, indamine, indanthrone, indigoid, indophenol, indoaniline, isoindoline, isoindolinone, isoviolanthrone, lactone, methine, naphthalimide, naphthanilide, naphtholactam, naphthoquinone, nitro, oxadiazole, oxazine, perilone, perinone, perylene, phenazine, phenothiazine, phthalocyanin, polyene/carotenoid, porphyrin, pyranthrone, pyrazolanthrone, pyrazolone, pyrimidinoanthrone, pyronine, quinacridone, quinoline, quinophthalone, squarane, stilbene, styryl, tetrazolium, thiazine, thioindigo, thiopyronine, triarylmethane and xanthene dyes.

In various embodiments, direct dyes include, but are not limited to, cationic direct dyes, such as cationic mixed dyes including at least one chromophore, such as at least two chromophores, including those described in U.S. Pat. Nos. 7,172,633 and 7,582,122, both of which are incorporated by reference herein. As used herein, "cationic mixed dye" means a dye whose cationic charge can form an integral part of the chromophore and/or of the linker, or alternatively a dye whose cationic charge is present via a substituent on the chromophore and/or on the linker. As used herein, "chromophore" means a radical derived from a dye, i.e. a radical of a molecule that has at least one absorption maximum in the visible region between 400 and 800 nm, this absorbance requiring no prior oxidation or any combination with other chemical species.

In various embodiments where the at least one dye is chosen from mixed cationic dyes, the at least one chromophore may be chosen from acridine, acridone, anthranthrone, anthrapyrimidine, anthraquinone, azine, azo, azomethine, benzanthrone, benzimidazole, benzimidazolone, benzindole, benzoxazole, benzopyran, benzothiazole, benzoquinone, bis-azine, bis-isoindoline, carboxanilide, coumarin, cyanins, diazine, diketopyrrolopyrrole, dioxazine, diphenylamine, diphenylmethane and dithiazine chromophores, flavonoids, fluorindines, formazans, hydrazones, hydroxy ketones, indamines, indanthrones, indigoids, pseudo-indigoids, indophenols, indoanilines, isoindolines, isoindolines, isoindolinones, isoviolanthrones, lactones, methines, naphthalimides, naphthanilides, naphtholactams, naphthoquinones, nitro dyes, oxadiazoles, oxazines, perilones, perinones, perylenes, phenazines, phenothiazines, phthalocyanin, polyenes/carotenoids, porphyrins, pyranthrones, pyrazolanthrones, pyrazolones, pyrimidinoanthrones, pyronines, quinacridones, quinolines, quinophthalones, squaranes, stilbenes, tetrazoliums, thiazines, thioindigo, thiopyronines, triarylmethanes, and xanthenes.

By way of example, cationic direct dyes may be chosen from compounds of formula (XIX):

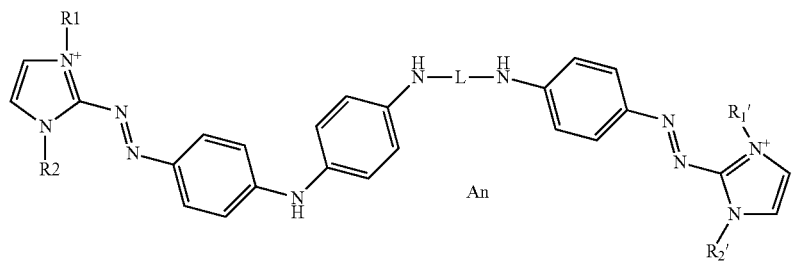

wherein, in formula (XIX):
- L is a linker chosen from cationic and non-cationic atoms or groups of atoms separating the chromophores from the mixed dye,
- R1 and R1' are independently chosen from an alkyl radical, for example $C_1$-$C_6$, optionally substituted with one or more hydroxyl, $C_1$-$C_2$ alkoxy, $C_2$-$C_4$ (poly) hydroxyalkoxy, amino, $C_1$-$C_2$ (di)alkylamino or optionally substituted aryl radicals, and
- R2 and R2' are independently chosen from a $C_1$-$C_6$ alkyl radical, optionally substituted with one or more hydroxyl, $C_1$-$C_2$ alkoxy, $C_2$-$C_4$ (poly)hydroxyalkoxy, amino, $C_1$-$C_2$ (di)alkylamino radicals; an optionally substituted phenyl radical; and
- An represents one or more identical or different, monovalent or multivalent anions.

By way of example, direct dyes of formula (XIII) that may be chosen include the following:

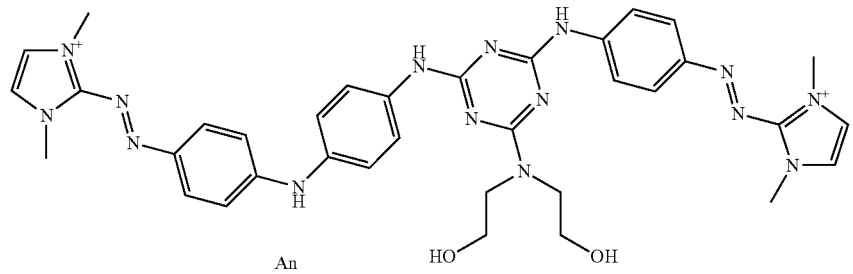

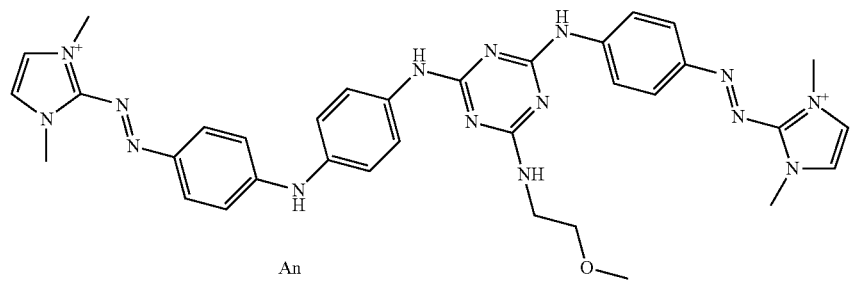

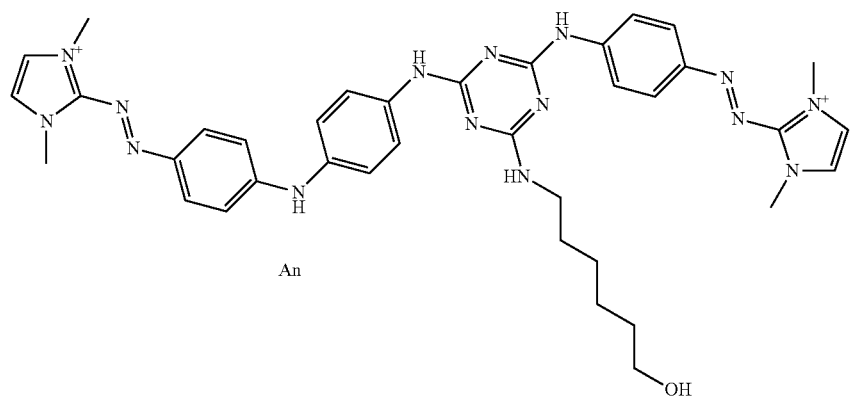

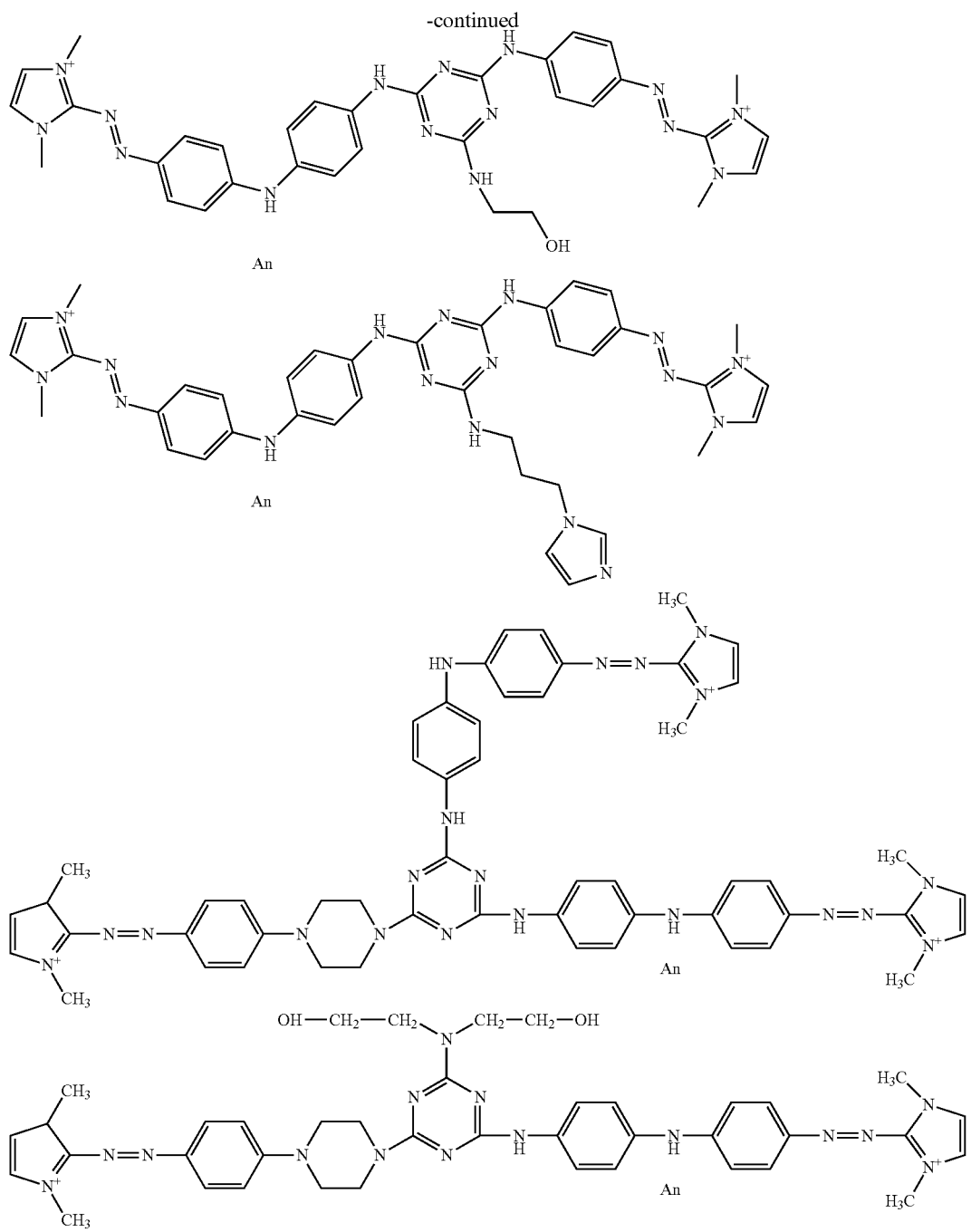

In further embodiments, the at least one direct dye may be chosen from dyes of formula (XX), such as those described in U.S. Pat. No. 7,220,286, incorporated by reference herein:

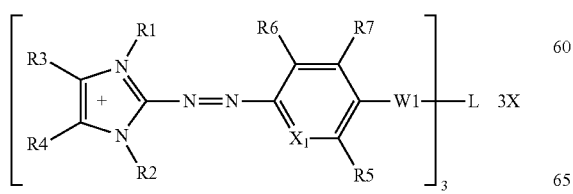

wherein, in formula (XX):

W1 is chosen from —NR8- or —O—;

X1 represents N or CR9;

R1 and R2, independently, are chosen from a hydrocarbon chain;

R3 and R4, independently, are chosen from a hydrogen atom, a halogen atom, a nitro group, a cyano group or a hydrocarbon chain;

R5 to R9, independently, are chosen from a hydrogen atom or a hydrocarbon chain; and L represents one of the groups chosen from the following:

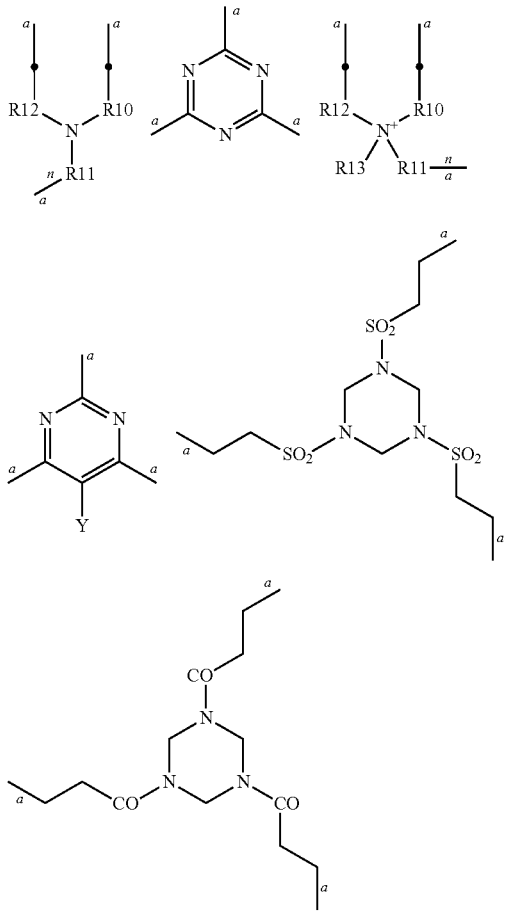

wherein:
R10 to R13, independently, are chosen from a hydrocarbon chain;
Y is chosen from a halogen atom, e.g. fluorine or chlorine;
the bond a is connected to the group W1 of formula (XX); and
X represents a cosmetically acceptable organic or mineral anion.

Direct dyes of formula (XX) also comprise a cosmetically acceptable anion that is organic or mineral in nature. By way of example of anions that are mineral in nature, mention may be made of halides, such as chlorides; hydroxides, sulphates; hydrogen sulphates. By way of examples of anions that are organic in nature, suitable anions are, for instance, acetate; citrate; tartrate; alkyl sulphates for which the linear or branched alkyl portion is a $C_1$-$C_6$ alkyl, such as the methosulphate or ethosulphate ion; alkylsulphonates for which the linear or branched alkyl portion is a $C_1$-$C_6$ alkyl; arylsulphonates for which the aryl, e.g. phenyl, portion is optionally substituted with one or more $C_1$-$C_4$ alkyl radicals.

Exemplary direct dyes of formula (XX) include, but are not limited to: 2-((E)-{4-[(3-{bis[3-({4-[(E)-(1,3-dimethyl-1H-imidazol-3-ium-2-yl)diazenyl]phenyl}amino)propyl]amino}propyl)amino]phenyl}diazenyl)-1,3-dimethyl-1H-imidazol-3-ium trichloride 2-{(E)-[4-({3-[bis[3-({4-[(E)-(1,3-dimethyl-1H-imidazol-3-ium-2-yl)diazenyl]phenyl}amino)propyl](methyl)ammonio]propyl}amino)phenyl]-diazenyl}-1,3-dimethyl-1H-imidazol-3-ium tetrachloride 2-((E)-{4-[{3-[bis{3-[{4-[(E)-(1,3-dimethyl-1H-imidazol-3-ium-2-yl)diazenyl]phenyl}(methyl)amino]propyl}(methyl)ammonio]propyl}(methyl)amino]phenyl}diazenyl)-1,3-dimethyl-1H-imidazol-3-ium tetrachloride 2-((E)-{4-[{3-[bis{3-[{4-[(E)-(1,3-diethyl-1H-imidazol-3-ium-2-yl)diazenyl]phenyl}(ethyl)amino]propyl}(ethyl)ammonio]propyl}(ethyl)amino]phenyl}dia-zenyl)-1,3-diethyl-1H-imidazol-3-ium tetrachloride 2-((E)-{4-[{3-[bis{3-[{4-((E)-(1,3-dimethyl-1H-imidazol-3-ium-2-yl)diazenyl]phenyl}(ethyl)amino]propyl}(ethyl)ammonio]propyl}(ethyl)amino]phenyl}di-azenyl)-1,3-dimethyl-1H-imidazol-3-ium tetrachloride 2-((E)-{4-[(3-{3,5-bis[3-({4-[(E)-(1,3-dimethyl-1H-imidazol-3-ium-2-yl)diazenyl]phenyl}amino)propanoyl]-1,3,5-triazinan-1-yl}-3-oxopropyl]amino]phenyl}diazenyl)-1,3-dimethyl-1H-imidazol-3-ium trichloride 2-((E)-{4-[[3-(3,5-bis{3-[{4-[(E)-(1,3-dimethyl-1H-imidazol-3-ium-2-yl)di-azenyl]phenyl}(ethyl)amino]propanoyl}-1,3,5-triazinan-1-yl)-3-oxopropyl](ethyl)amino]phenyl}diazenyl)-1,3-dimethyl-1H-imidazol-3-ium trichloride 2-{(E)-[4-({2-[(3,5-bis{[2-({4-[(E)-(1,3-dimethyl-1H-imidazol-3-ium-2-yl)-diazenyl]phenyl}amino)ethyl]sulphonyl}-1,3,5-triazinan-1-yl)sulphonyl]ethyl]amino)phenyl]diazenyl}-1,3-dimethyl-1H-imidazol-3-ium trichloride 2-((E)-{4-[(2-{[3,5-bis({2-[{4-[(E)-(1,3-dimethyl-1H-imidazol-3-ium-2-yl)-diazenyl]phenyl}(ethyl)amino]ethyl}sulphonyl)-1,3,5-triazinan-1-yl]sulphonyl}ethyl)(ethyl)amino]phenyl}diazenyl)-1,3-dimethyl-1H-imidazol-3-ium trichloride 2-[(E)-(4-{[4,6-bis({4-[(E)-(1,3-dimethyl-1H-imidazol-3-ium-2-yl)diazenyl-]phenyl}amino)-1,3,5-triazin-2-yl]amino}phenyl)diazenyl]-1,3-dimethyl-1H-i-midazol-3-ium trichloride 2-((E)-{4-[{4,6-bis[{4-[(E)-(1,3-dimethyl-1H-imidazol-3-ium-2-yl)diazenyl-]phenyl}(methyl)amino]-1,3,5-triazin-2-yl}(methyl)amino]phenyl}diazenyl)-1-,3-dimethyl-1H-imidazol-3-ium trichloride 2-[(E)-(4-{[5 Chloro-2,6-bis({4-[(E)-(1,3-dimethyl-1H-imidazol-3-ium-2-yl)diazenyl]phenyl}amino)pyrimidin-4-yl]amino}phenyl)diazenyl]-1,3-dimethyl-1H-imidazol-3-ium trichloride 2-((E)-{4-[{5 Chloro-2,6-bis[{4-[(E)-(1,3-dimethyl-1H-imidazol-3-ium-2-yl)diazenyl]phenyl}(methyl)amino]pyrimidin-4-yl}(methyl)amino]-phenyl}diazenyl)-1,3-dimeth-yl-1H-imidazol-3-ium trichloride.

In various exemplary embodiments, the at least one direct dye is chosen from hydroxyethyl-2-nitro-p-toluidine and 3-methylamino-4-nitrophenoxyethanol.

In various embodiments, the at least one direct dye may be present in an amount ranging from about 0.001% to about 20% by weight, such as from about 0.005% to about 10% by weight, or from about 0.01% to about 5% by weight, based on the total weight of the color-altering composition.

The color-altering composition may optionally comprise at least one chemical oxidizing agent chosen from peroxides, persulfates, perborates, percarbonates, peracids, bromates, their salts and mixtures thereof. The at least one chemical oxidizing agent may, optionally, be water-soluble.

Optional peroxides useful herein include, for example, hydrogen peroxide, magnesium peroxide, PVP-peroxide, calcium peroxide, and sodium peroxide. In other embodiments, the color-altering composition does not comprise a chemical oxidizing agent. In such cases, the composition may be optionally oxidized by environmental circumstances, e.g., air may serve as the oxidizing agent.

According to one embodiment, the color-altering composition does not contain any, or contains substantially no, peroxide, such as hydrogen peroxide (H2O2). Peroxides, such as hydrogen peroxide, are known in the art as potentially damaging to the hair fibers, particularly when left in contact with the fibers for extended periods of time during dyeing processes. It would therefore be advantageous to provide a dyeing process that does not employ peroxides, for instance, a dyeing process wherein the color-altering composition does not comprise peroxides, such as hydrogen peroxide.

Exemplary, non-limiting persulfates include potassium persulfate, sodium persulfate, and ammonium persulfate. In various embodiments, exemplary oxidizing agents may be chosen from sodium perborate and sodium percarbonate. In further embodiments, exemplary peracids may be chosen from organic peracids having the general formula (I):

wherein, in formula (I), R is chosen from saturated or unsaturated, substituted or unsubstituted, straight or branched chain, alkyl, aryl or alkaryl groups having from 1 to 22 carbon atoms. In at least some exemplary embodiments, mixtures of two or more oxidizing agents chosen from persulfates, perborates, percarbonates, peracids, bromates, and salts thereof, may be chosen.

In various embodiments, the at least one chemical oxidizing agent is chosen from alkali metal salts of perborates, percarbonates, bromates, and persulfates, such as, for example, ammonium, sodium, and potassium salts. In further embodiments, the color-altering composition comprises substantially no chemical oxidizing agent, and in yet further embodiments, the color-altering composition does not comprise a chemical oxidizing agent.

The color-altering composition may optionally further comprise at least one oxidative dye precursor. Useful oxidative dye precursors include, by way of example only, aromatic diamines, polyhydric phenols, amino phenols, and derivatives of these compounds, such as, for example, N-substituted derivatives of the amines, and ethers of the phenols.

By way of non-limiting example, oxidative dye precursors may be chosen from ortho- or para-aminophenols, ortho- or para-phenylenediamines, double bases, heterocyclic bases, and the acid addition salts thereof.

Exemplary para-phenylenediamines which may be chosen include compounds of the general formula (XXIII) and their addition salts with an acid:

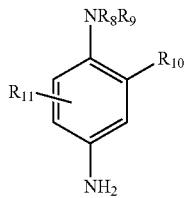

wherein, in formula (XXIII):
R8 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical, a C1-C4 alkyl radical substituted by a nitrogenous group, a phenyl radical or a 4'-aminophenyl radical;
R9 represents a hydrogen atom, a C1-C4 alkyl radical, a C1-C4 monohydroxyalkyl radical, a C2-C4 polyhydroxyalkyl radical, a (C1-C4)alkoxy(C1-C4)alkyl radical or a C1-C4 radical substituted by a nitrogenous group;
R8 and R9 can also form, with the nitrogen atom which carries them, a 5- or 6-membered nitrogenous heterocycle optionally substituted by one or more alkyl, hydroxyl or ureido groups;
R10 represents a hydrogen atom, a halogen atom, such as a chlorine atom, a C1-C4 alkyl radical, a sulpho radical, a carboxyl radical, a C1-C4 monohydroxyalkyl radical, a C1-C4 hydroxyalkoxy radical, a C1-C4 acetylaminoalkoxy radical, a C1-C4 mesylaminoalkoxy radical or C1-C4 carbamoylaminoalkoxy radicals; and
R11 represents a hydrogen atom, a halogen atom or a C1-C4 alkyl radical.

By way of example, among the nitrogenous groups in the above formula (XXIII), of the amino, mono(C1-C4)alkylamino, di(C1-C4)alkylamino, tri(C1-C4)alkylamino, monohydroxy(C1-C4)alkylamino, imidazolinium and ammonium radicals may be chosen. Exemplary para-phenylenediamines of above formula (XXIII), include para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(beta-hydroxyethyl)-para-phenylenediamine, 4-N,N-bis(beta-hydroxyethyl)amino-2-methylaniline, 4-N,N-bis(beta-hydroxyethyl)amino-2-chloroaniline, 2-(beta-hydroxyethyl)-para-phenylenediamine, 2-fluoro-para-phenylenediamine, 2-isopropyl-para-phenylenediamine, N-(beta-hydroxypropyl)-para-phenylenediamine, 2-hydroxymethyl-para-phenylenediamine, N,N-dimethyl-beta-methyl-para-phenylenediamine, N-ethyl-N-(beta-hydroxyethyl)-para-phenylenediamine, N-(beta,gamma-dihydroxypropyl)-para-phenylenediamine, N-(4'-aminophenyl)-para-phenylenediamine, N-phenyl-para-phenylenediamine, 2-((beta-hydroxyethyloxy)-para-phenylenediamine, 2-((beta-acetylaminoethyloxy)-para-phenylenediamine, N-(beta-methoxyethyl)-para-phenylenediamine, 2-methyl-1-N-(beta-hydroxyethyl)-para-phenylenediamine and their addition salts with an acid.

Exemplary ortho-phenylenediamines, include N1-(2-hydroxyethyl)-4-nitro-o-phenylenediamine, 4-methyl-o-phenylenediamine, and 4-nitro-o-phenylenediamine and acid addition salts thereof.

As used herein, the term "double bases" means compounds comprising at least two aromatic nuclei having at least one of amino and hydroxyl groups. For example, double bases may be chosen from compounds of the formula (XXIV) and their addition salts with an acid:

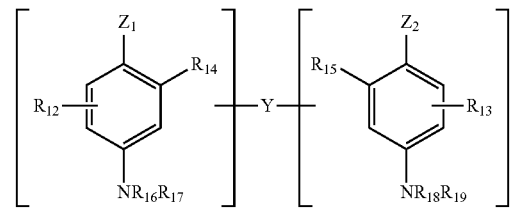

wherein, in formula (XXIV):
Z1 and Z2 may independently be chosen from a hydroxyl or —NH2 radical which can be substituted by a C1-C4 alkyl radical or by a connecting arm Y;
the connecting arm Y is chosen from a linear or branched alkylene chain comprising from 1 to 14 carbon atoms which can be interrupted or terminated by one or more nitrogenous groups and/or by one or more heteroatoms, such as oxygen, sulphur or nitrogen atoms, and which is optionally substituted by one or more hydroxyl or C1-C6 alkoxy radicals;

R12 and R13 are independently chosen from a hydrogen or halogen atom, a C1-C4 alkyl radical, a C1-C4 monohydroxyalkyl radical, a C2-C4 polyhydroxyalkyl radical, a C1-C4 aminoalkyl radical or a connecting arm Y;

R14, R15, R16, R17, R18 and R19 are independently chosen from a hydrogen atom, a connecting arm Y or a C1-C4 alkyl radical;

wherein compounds of formula (XXIV) only comprise a single connecting arm Y per molecule.

In various embodiments, nitrogenous groups of the above formula (XXIV), may be chosen from amino, mono(C1-C4) alkylamino, di(C1-C4)alkylamino, tri(C1-C4)alkylamino, monohydroxy(C1-C4)alkylamino, imidazolinium and ammonium radicals.

Nonlimiting examples of double bases include N,N'-bis (beta-hydroxyethyl)-N,N'-bis(4'-aminophenyl)-1,3-di-amino-propan-ol, N,N'-bis(beta-hydroxyethyl)-N,N'-bis(4'-aminophenyl)ethylenediamine, N,N'-bis(beta-aminophenyl)-tetramethylenediamine, N,N'-bis(4-hydroxyethyl)-N,N'-bis(4-aminophenyl) tetramethylenediamine, N,N'-bis(4-methylaminophenyl) tetramethylenediamine, N,N'-diethyl-N,N'-bis(4'-amino-3'-methylphenyl)ethylenediamine, 1,8-bis(2,5-diamino-phenoxy)-3,5-dioxaoctane, and their addition salts with an acid.

Non-limiting examples of para-aminophenols which can be used in the context of the invention can be chosen in particular from the compounds corresponding to the following formula (XXV): and their addition salts with an acid:

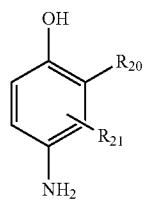

wherein, in formula (XXV):

R20 is chosen from a hydrogen atom, a halogen atom, such as fluorine, a C1-C4 alkyl radical, a C1-C4 monohydroxyalkyl radical, a (C1-C4)alkoxy(C1-C4) alkyl radical, a C1-C4 aminoalkyl radical or a hydroxy (C1-C4)alkylamino-(C1-C4)alkyl radical, and R21 is chosen from a hydrogen atom, a halogen atom, such as fluorine, a C1-C4 alkyl radical, a C1-C4 monohydroxyalkyl radical, a C2-C4 polyhydroxyalkyl radical, a C1-C4 aminoalkyl radical, a C1-C4 cyano-alkyl radical or a (C1-C4) alkoxy(C1-C4) alkyl radical.

By way of example only, para-aminophenol, 4-amino-3-methylphenol, 4-amino-3-fluorophenol, 4-amino-3-hydroxymethylphenol, 4-amino-2-methylphenol, 4-amino-2-hydroxymethyl phenol, 4-amino-2-methoxymethylphenol, 4-amino-2-aminomethylphenol, 4-amino-2-(beta-hydroxy-ethylaminomethyl)phenol, N-methyl-para-aminophenol, and the acid addition salts thereof may be chosen.

Exemplary ortho-aminophenols may be chosen from 2-aminophenol, 2-amino-1-hydroxy-5-methylbenzene, 2-amino-1-hydroxy-6-methylbenzene, 5-acetamido-2-aminophenol, and the acid addition salts thereof.

Exemplary heterocyclic bases may be chosen from pyridine derivatives, pyrimidine derivatives, pyrazole derivatives, pyrazolinone derivatives, and the acid addition salts thereof.

Non-limiting examples of pyridine derivatives include, for example, those disclosed in GB1026978 and GB1153196, both incorporated by reference herein, such as 2,5-diaminopyridine, 2-(4-methoxyphenyl)amino-3-aminopyridine, 2,3-diamino-6-methoxypyridine, 2-(beta-methoxyethyl)amino-3-amino-6 methoxypyridine, 3,4-diaminopyridine, and the acid addition salts thereof.

Non-limiting examples of pyrimidine derivatives include, for example, those described in DE 2 359 399, JP 63-169571, JP 91-10659 and WO 96/15765, all incorporated by reference herein, such as 2,4,5,6-tetra-aminopyrimidine, 4-hydroxy-2,5,6-triaminopyrimidine, 2-hydroxy-4,5,6-tri-amino-pyrimidine, 2,4-dihydroxy-5,6-diaminopyrimidine, 2,5,6-triaminopyrimidine, and the pyrazolopyrimidine derivatives, such as those mentioned in French Application FRA-2 750 048 and among which may be mentioned pyrazolo[1,5-a]pyrimidine-3,7- diamine; 2,5-dimethylpyrazolo[1,5-a]pyrimidine-3,7 -diamine; pyrazolo[1,5-a]pyrimidine-3,5-diamine; 2,7 -dimethylpyrazolo[1,5-a]pyrimidine-3,5-diamine; 3-aminopyrazolo[1,5-a]pyrimidin-7 -01; 3-aminopyrazolo[1,5-a]pyrimidin-5-01; 2-(3-aminopyrazolo[1,5-a]pyrimidin-7-ylamino)ethanol; 2-(7-aminopyrazolo[1,5-a]pyrimidin-3-ylamino)ethanol; 2-[(3-aminopyrazolo[1,5-a]pyrimidin-7-yl)(2-hydroxyethyl)aminolethanol; 2-[(7-aminopyrazolo[1,5-a]pyrimidin-3-yl)(2-hydroxyethyl)amino]ethanol; 5,6-dimethyl-pyrazolo[1,5-a]pyrimidine-3,7-diamine; 2,6-dimethylpyrazolo[1,5-a]pyrimidine-3,7-diamine; 2,5,N7,N7-tetramethylpyrazolo[1,5-a]pyrimidine-3,7-diamine; 3-amino-5-methyl-7-(imidazolylpropylamino)pyrazolo[1,5-a]pyrimidine; and their addition salts and their tautomeric forms, when there exists a tautomeric equilibrium, and their addition salts with an acid.

Non-limiting examples of pyrazole and pyrazolinone derivatives include the compounds described in DE 3,843, 892, DE 4,133,957, WO 94/08969, WO 94/08970, FR-A-2,733,749, and DE 195 43 988, all of which are incorporated by reference herein, such as 4,5-diamino-1-methyl-pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(beta-hydroxyethyl)-3-methylpyrazole, 4,5-diamino-1-(beta-hydroxyethyl)pyrazole, 4,5-diamino-1-ethyl-3-methylpyrazole, 4,5-diamino-1-ethyl-3-(4'-methoxyphenyl) pyrazole, 4,5-diamino-1-ethyl-3-hydroxymethylpyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl) amino-1,3-dimethyl-pyrazole, 3,4,5-triaminopyrazole, 1-methyl-3,4,5-triaminopyrazole, 3,5-diamino-1-methyl-4-methylaminopyrazole, 3,5-diamino-4-(p-hydroxyethyl) amino-1-methylpyrazole, 2-(4,5-diamino-1H-pyrazol-1-yl), $H_2SO_4$, 2,3-diamino-6,7-dihydro-1H,5H-pyrazolo[1,2-z] pyrazol-1-one, 1-methyl-3-phenyl-2-pyrazolinone, and the acid addition salts thereof.

The at least one oxidation dye precursor may be present in an amount ranging from, for example, about 0.0001% to about 12%, such as from about 0.0001% to about 8.0%, or from about 0.005% to about 5% by weight, based on the total weight of the composition.

The color-altering composition may optionally further comprise at least one lift-enhancing agent. Lift-enhancing agents that may be useful in the color-altering composition include those that are capable of generating ammonia. By way of example only, lift-enhancing agents may be chosen from ammonium salts, amino acids, and urea and derivatives thereof.

Exemplary ammonium salts may be chosen from ammonium chloride, ammonium sulphate, ammonium nitrate, ammonium phosphate, ammonium acetate, ammonium carbonate, ammonium hydrogen carbonate, ammonium carbamate, and mixtures thereof.

Quaternary ammonium or diammonium salts may optionally be used. By way of example only, those described in US2005071933, incorporated by reference herein, may be chosen, such as, for example, those of the general formula (XXI):

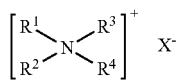

wherein, in formula (XXI):
R1 and R4, may independently be chosen from saturated or unsaturated, linear or branched, aliphatic hydrocarbon radicals comprising from 1 to about 30 carbon atoms, or an alkoxy, alkoxycarbonylalkyl, polyoxyalkylene, alkylamido, alkylamidoalkyl, hydroxyalkyl, aromatic, aryl or alkylaryl radical comprising from about 12 to about 30 carbon atoms, with at least one radical among R1, R2, R3 and R4 denoting a radical comprising from 8 to 30 carbon atoms; and —X⁻ is an anion chosen from the group comprising halides, phosphates, acetates, lactates and alkyl sulphates;
and/or general formula (XXII):

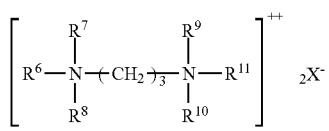

wherein, in formula (XXII):
R6 denotes an aliphatic radical comprising from about 16 to 30 carbon atoms,
R7, R8, R9, R10 and R11 are independently chosen from hydrogen or an alkyl radical comprising from 1 to 4 carbon atoms, and
X⁻ is an anion chosen from the group comprising halides, acetates, phosphates and sulphates.

Quaternary ammonium and diammonium salts include, for example, distearyldimethylammonium chloride, cetyltrimethylammonium chloride, behenyltrimethylammonium chloride, oleocetyldimethylhydroxyethylammonium chloride, stearamidopropyldimethyl (myristyl acetate) ammonium chloride, di($C_1$-$C_2$ alkyl)($C_{12}$-$C_{22}$ alkyl)hydroxy($C_1$-$C_2$alkyl)ammonium salt, such as dialkyldimethylammonium or alkyltrimethylammonium salt in which the alkyl radical comprises 12 to 22 carbon atoms, and propanetallowdiammonium dichloride.

Imidazolium salts may also be used, such as, for example, the product sold as REWOQUAT W 7500 by the company REWO.

As examples of amino acids that may be chosen, mention may be made of aspartic acid, glutamic acid, alanine, arginine, ornithine, citrulline, asparagine, carnitine, cysteine, glutamine, glycine, histidine, lysine, isoleucine, leucine, methionine, N-phenylalanine, proline, serine, taurine, threonine, tryptophan, tyrosine and valine.

In various embodiments, the at least one lift-enhancing agent may be present in an amount ranging from about 0.01% to about 10% by weight, such as from about 0.05% to about 5% by weight, based on the total weight of the composition.

The color-altering composition may also comprise a cosmetically acceptable carrier. The cosmetically acceptable carrier may, for example, be present in the color-altering composition in an amount ranging from about 1% to about 40% by weight, such as from about 5% to about 35% by weight, or about 10% to about 30% by weight of the color-altering composition.

Auxiliary ingredients may be added to the color-altering composition. Exemplary auxiliary ingredients useful in the color-altering composition according to various embodiments of the disclosure include, but are not limited to, rheology-modifying agents, activators, chelants, fatty substances, ceramides, alkoxyaminosilicones, and silanes, and lift-enhancing agents chosen from metal catalyst compounds.

The color-altering composition may also contain acid and alkali pH adjusters, which are well known in the art in the cosmetic treatment of keratin fibers, such as hair. Such pH adjusters include, but are not limited to, sodium metasilicate, silicate compounds, citric acid, ascorbic acid, and carbonate compounds.

The pH adjusters may, in various embodiments, be present in the color-altering composition in an amount effective to provide the color-altering composition with a pH of not greater than 7, such as a pH ranging from about 1 to about 7, from about 2 to about 6, or from about 3 to about 5. By way of example, the amount of pH adjuster may be present, in various embodiments, in an amount of at least about 0.01%, such as at least about 0.1%, at least about 0.2%, or at least about 0.5%.

The color-altering composition may be left on the hair for a period of time sufficient to achieve the desired alteration in hair tone/color. For example, the color-altering composition may be left on the hair for up to one hour, such as from about 3 minutes to about 45 minutes, from about 5 minutes to about 30 minutes, or from about 10 minutes to about 20 minutes. In further embodiments, the color-altering composition may be left on the hair for a period up to about 30 minutes, such as, for example, from about 1 to about 30 minutes, about 1 to about 10 minutes, or about 1 to about 5 minutes. One skilled in the art will, by considering various factors such as the starting and desired color of the hair, be able to determine an appropriate amount of time to leave the color-altering composition on the hair in order to achieve the desired alternation in hair color.

If desired, the color-altering composition may, optionally, be rinsed off the hair.

Post-Treatment Composition

Optionally, in at least some exemplary embodiments, a post-treatment composition may be applied to the hair. The post-treatment step may be performed at any time subsequent to the pre-alkalizing and color-altering steps.

The post-treatment composition may be any composition for treating hair, and may include, for example, a conditioning composition, a permanent waving composition, a straightening composition, and/or a composition for coloring the hair. The post-treatment composition may be in any form, such as, for example, the form of a shampoo, a rinse conditioner, a non-rinse conditioner, or a leave-on treatment composition.

In at least one exemplary embodiment, the post-treatment composition may be chosen from a surfactant-based composition. The surfactant-based composition may contain at least one surfactant chosen from anionic, amphoteric, nonionic, zwitterionic, and cationic surfactants, and mixtures thereof. The exemplary surfactant-based composition may also comprise a cosmetically acceptable carrier.

The at least one surfactant in the surfactant-based composition may be present in an amount ranging from about 0.01% to about 40%, such as from about 0.05% to about 30%, relative to the total weight of the surfactant-based composition.

In various exemplary embodiments, the post-treatment composition may optionally further comprise at least one auxiliary ingredient. Exemplary auxiliary ingredients that may be useful in the post-treatment composition according to various embodiments of the disclosure include, but are not limited to, rheology-modifying agents, chelants, fatty substances, ceramides, alkoxyaminosilicones, and silanes.

Cosmetically Acceptable Carrier

Cosmetically acceptable carriers useful according to various embodiments described herein may, by way of non-limiting example, be chosen from water, organic solvents, natural oils, synthetic oils, esters, hydrocarbons, silicones, and mixtures thereof. Non-limiting examples of cosmetically acceptable carriers include alcohols, such as ethanol, isopropyl alcohol, benzyl alcohol and phenyl ethyl alcohol; glycols and glycol ethers, such as propylene glycol, hexylene glycol, ethylene glycol monomethyl, monoethyl or monobutyl ether, propylene glycol and its ethers, such as propylene glycol monomethyl ether, butylene glycol, dipropylene glycol, and also diethylene glycol alkyl ethers, such as diethylene glycol monoethyl ether and monobutyl ether; hydrocarbons such as straight chain hydrocarbons, mineral oil, polybutene, hydrogenated polyisobutene, hydrogenated polydecene, polydecene, squalene, petrolatum and isoparaffins; and mixtures thereof, to name a few.

Auxiliary Ingredients

The pre-alkalizing composition, the color-altering composition, and/or the post-treatment composition may, optionally, comprise one or more auxiliary ingredients chosen from rheology-modifying agents, activators, direct dyes, chelants, fatty substances, ceramides, alkoxyaminosilicones, silanes, and lift-enhancing agents, such as nitrogen-containing compounds and metal catalyst compounds. It is to be understood that various compounds can serve more than one intended purpose. For example, amino acids such as glycine may act as both a lift-enhancing agent and an activator.

Rheology-Modifying Agents

Exemplary rheology-modifying agents that may be used according to the disclosure include, but are not limited to, nonionic, anionic, cationic, or amphoteric polymers, and other rheology modifiers such as cellulose-based thickeners (e.g. hydroxyethylcellulose, hydroxypropylcellulose, carboxymethylcellulose, cationic cellulose ether derivatives, quaternized cellulose derivatives, etc.), guar gum and its derivatives (e.g. hydroxypropyl guar, cationic guar derivatives, etc.), gums of microbial origin (e.g. xanthan gum, scleroglucan gum, etc.), crosslinked homopolymers of acrylic acid or of acrylamidopropane-sulfonic acid, associative polymers, non-associative thickening polymers, and water-soluble thickening polymers, as described below.

In various exemplary embodiments, the compositions according to the disclosure may comprise at least one polymer chosen from nonionic, anionic, cationic or amphoteric amphiphilic polymers.

The amphiphilic polymers may, optionally, contain a hydrophobic chain that is a saturated or unsaturated, aromatic or non-aromatic, linear or branched $C_6$-$C_{30}$ hydrocarbon-based chain, optionally comprising one or more oxyalkylene (oxyethylene and/or oxypropylene) units.

Exemplary, non-limiting cationic amphiphilic polymers comprising a hydrophobic chain that may be chosen are cationic polyurethanes or cationic copolymers comprising vinyllactam units, such as vinylpyrrolidone units.

As non-limiting examples of nonionic amphiphilic polymers containing a hydrophobic chain, mention may be made, inter alia, of:

(1) celluloses modified with groups comprising at least one saturated or unsaturated, linear or branched $C_6$-$C_{30}$ hydrocarbon-based chain, for instance hydroxyethylcelluloses modified with groups comprising at least one hydrophobic chain as defined previously, such as especially Natrosol Plus Grade 330 CS ($C_{16}$ alkyls—sold by the company Aqualon); Bermocoll EHM 100 (sold by the company Berol Nobel), Amercell Polymer HM-1500 (hydroxyethylcellulose modified with a polyethylene glycol (15) nonylphenyl ether group-sold by the company Amerchol);

(2) hydroxypropyl guars modified with groups comprising at least one hydrophobic chain as defined, for example Jaguar XC-95/3 ($C_{14}$ alkyl chain-sold by the company Rhodia Chimie); Esaflor HM 22 ($C_{22}$ alkyl chain-sold by the company Lamberti); RE210-18 ($C_{14}$ alkyl chain) and RE205-1 ($C_{20}$ alkyl chain-sold by the company Rhodia Chimie);

(3) copolymers of vinylpyrrolidone and of hydrophobic monomers containing a hydrophobic chain as defined above, for instance Antaron or Ganex V216 (vinylpyrrolidone/hexadecene copolymers); Antaron or Ganex V220 (vinylpyrrolidone/eicosene copolymers), sold by the company I.S.P.;

(4) copolymers of $C_1$-$C_6$ alkyl(meth)acrylates and of amphiphilic monomers containing a hydrophobic chain;

(5) copolymers of hydrophilic (meth)acrylates and of hydrophobic monomers comprising at least one hydrophobic chain, for instance the polyethylene glycol methacrylate/lauryl methacrylate copolymer;

(6) polymers with an aminoplast ether skeleton containing at least one fatty chain, such as the Pure Thix compounds sold by the company Sud-Chemie;

(7) linear (block structure), grafted, or starburst polyurethane polyethers comprising in their chain at least one hydrophilic block, which is generally a polyoxyethylene block which may comprise between 50 and 1000 oxyethylene units approximately, and at least one hydrophobic block, which may comprise aliphatic groups alone, optionally combined with cycloaliphatic and/or aromatic blocks. In various embodiments, the polyurethane polyethers comprise at least two $C_6$-$C_{30}$ hydrocarbon-based hydrophobic chains, separated by a hydrophilic block; the hydrophobic chains may be pendent chains or chains with one or more of the end groups of the hydrophilic block(s).

The polyurethane polyethers may comprise a urethane bond between the hydrophilic blocks, but may also contain hydrophilic blocks linked to the lipophilic blocks via other chemical bonds. Examples of polyurethane polyethers that may be used include, but are not limited to, Nuvis FX 1100 (European and US INCI name "Steareth-100/PEG-136/HMDI Copolymer" sold by the company Elementis Specialties); Rheolate® 205, 208, 204 or 212 (sold by the company Rheox) and also Acrysol RM 184® (sold by the company Rohm & Haas); Elfacos T210® ($C_{12}$-$C_{14}$ alkyl chain) and Elfacos T212® ($C_{18}$ alkyl chain) sold by the company Akzo. The product DW 1206B® from Rohm and Haas comprising a $C_{20}$ alkyl chain and comprising a urethane bond, provided at a solids content of 20 percent in water, can also be used.

Use may also be made of solutions or dispersions of these polymers, for example in water or in an aqueous/alcoholic medium, such as polymers of Rheolate® 255, Rheolate® 278 and Rheolate® 244, sold by Rheox, and DW 1206F and DW 1206J provided by Rohm and Haas.

The anionic amphiphilic polymers containing a hydrophobic chain that may be used may comprise, as hydrophobic chain, at least one saturated or unsaturated, aromatic or non-aromatic, linear or branched $C_8$-$C_{30}$ hydrocarbon-based chain.

More particularly, the anionic amphiphilic polymers comprising at least one hydrophobic chain which are crosslinked or non-crosslinked, comprise at least one hydrophilic unit derived from one or more ethylenically unsaturated monomers bearing a carboxylic acid function, or a sulphonic function which is free or partially or totally neutralized, and at least one hydrophobic unit derived from one or more ethylenically unsaturated monomers bearing a hydrophobic side chain, and optionally at least one crosslinking unit derived from one or more polyunsaturated monomers.

The amphiphilic polymers may also optionally comprise at least one sulphonic group, in free or partially- or totally-neutralized form, and at least one hydrophobic portion.

Among these, mention may be made, by way of example, of acrylamido-2-methyl-2-propanesulphonic (AMPS) acid/n-dodecylacrylamide copolymer neutralized with sodium hydroxide, the copolymer crosslinked with methylenebisacrylamide consisting of 75% by weight of AMPS units neutralized by $NH_3$ and 25% by weight of Genapol® T-250 acrylate units, the copolymer crosslinked with allyl methacrylate consisting of 90% by weight of AMPS units neutralized with $NH_3$ and 10% by weight of Genapol® T-250 methacrylate units, or the copolymer crosslinked with allyl methacrylate consisting of 80% by weight of AMPS units neutralized with $NH_3$ and 20% by weight of Genapol® T-250 methacrylate units.

Other non-limiting examples include Carbopol® ETD-2020 (acrylic acid/$C_{10}$-$C_{30}$ alkyl methacrylate crosslinked copolymer sold by the company Noveon); Carbopol® 1382, Pemulen TR1 and Pemulen TR2 (acrylic acid/$C_{10}$-$C_{30}$ alkyl acrylate crosslinked copolymers-sold by the company Noveon), the methacrylic acid/ethyl acrylate/oxyethylenated stearyl methacrylate copolymer (55/35/10); the (meth) acrylic acid/ethyl acrylate/25 EO oxyethylenated behenyl methacrylate copolymer (ACULYN® 28 sold by Rohm & Haas) and the methacrylic acid/ethyl acrylate/steareth-10 allyl ether crosslinked copolymer.

Other suitable examples include anionic thickening polymers chosen from crosslinked terpolymers of methacrylic acid, ethyl acrylate, and polyethylene glycol (10 EO) stearyl alcohol ether (Steareth 10), such as the products sold by the company ALLIED COLLOIDS under the names SAL-CARE® SC 80 and SALCARE® SC 90, which are aqueous emulsions comprising 30% of a crosslinked terpolymer of methacrylic acid, of ethyl acrylate and of steareth-10-allyl ether (40/50/10).

Anionic thickening polymers comprising at least one fatty chain can also be chosen from: (1) terpolymers formed from maleic anhydride/$C_{30}$-$C_{38}$ alpha-olefin/alkyl maleate such as the product (maleic anhydride/$C_{30}$-$C_{38}$ alpha-olefin/isopropyl maleate copolymer) sold under the name PERFORMA® 1608 by the company NEWPHASE TECHNOLOGIES™, (2) acrylic terpolymers formed from: (a) 20% to 70% by weight of a carboxylic acid with α,β-monoethylenic unsaturation; (b) 20% to 80% by weight of a nonsurfactant monomer with α,β-monoethylenic unsaturation different from (a); (c) 0.5% to 60% by weight of a nonionic monourethane which is the product of the reaction of a monohydric surfactant with a monoisocyanate with monoethylenic unsaturation, (3) copolymers formed from at least two monomers, wherein at least one of said at least two monomers is chosen from a carboxylic acid with α,β-monoethylenic unsaturation, an ester of a carboxylic acid with α,β-monoethylenic unsaturation, and an oxyalkylenated fatty alcohol; and (4) copolymers formed from at least three monomers, wherein at least one of said at least three monomers is chosen from a carboxylic acid with α,β-monoethylenic unsaturation, at least one of said at least three monomers is chosen from an ester of a carboxylic acid with α,β-monoethylenic unsaturation and at least one of said at least three monomers is chosen from an oxyalkylenated fatty alcohol.

Additionally, these compounds can also comprise, as monomer, a carboxylic acid ester comprising an α,β-monoethylenic unsaturation and a $C_1$-$C_4$ alcohol. By way of example of this type of compound, there may be mentioned ACULYN® 22 sold by the company ROHM and HAAS, which is an oxyalkylenated stearyl methacrylate/ethyl acrylate/methacrylic acid terpolymer.

When the compositions according to various embodiments of the disclosure comprise one or more amphiphilic polymer(s) containing a hydrophobic chain, then this or these polymer(s) generally represent(s) from about 0.01% to about 20% by weight, such as, for example, from about 0.05% to about 10% by weight of the total weight of each composition.

The rheology modifier(s) that may be chosen according to various embodiments of the disclosure include polymers of natural origin and synthetic polymers, and may optionally be chosen from those conventionally used in cosmetics Non-limiting examples of synthetic polymers that may be used include polyvinylpyrrolidone, polyacrylic acid, polyacrylamide, non-crosslinked poly(2-acryl-amidopropanesulphonic acid) (Simugel™ EG from the company SEPPIC), crosslinked poly(2-acrylamido-2-methylpropanesulphonic acid), free or partially neutralized with ammonia (Hostacerin® AMPS from Clariant), mixtures of non-crosslinked poly(2-acrylamido-2-methylpropanesulphonic acid) with hydroxyalkylcellulose ethers or with poly(ethylene oxide)s, such as described in U.S. Pat. No. 4,540,510; mixtures of poly((meth)acrylamido($C_1$-$C_4$)alkylsulphonic acid), which is optionally crosslinked, with a crosslinked copolymer of maleic anhydride and of a ($C_1$-$C_5$)alkyl vinyl ether (Hostacerin® AMPS/Stabileze QM from the company ISF).

The polymers of natural origin may include, for example, thickening polymers comprising at least one sugar unit, for instance nonionic guar gums, optionally modified with $C_1$-$C_6$ hydroxyalkyl groups; biopolysaccharide gums of microbial origin, such as scleroglucan gum or xanthan gum; gums derived from plant exudates, such as gum arabic, ghatti gum, karaya gum, gum tragacanth, carrageenan gum, agar gum and carob gum; pectins; alginates; starches; hydroxy($C_1$-$C_6$)alkylcelluloses and carboxy($C_1$-$C_6$)alkylcelluloses.

It should be noted that the term "sugar unit" denotes a monosaccharide (i.e. monosaccharide or oside or simple sugar) portion, an oligosaccharide portion (short chains formed from a sequence of monosaccharide units, which may be different) or a polysaccharide portion [long chains consisting of monosaccharide units, which may be different, i.e. polyholosides or polyosides]. The saccharide units may also be substituted with alkyl, hydroxyalkyl, alkoxy, acyloxy or carboxyl radicals, the alkyl radicals containing from 1 to 4 carbon atoms.

Non-limiting examples of nonionic, unmodified guar gums that may be used in various embodiments include Guargel D/15 (Noveon); Vidogum GH 175 (Unipectine), Meypro-Guar 50 and Jaguar C (Meyhall/Rhodia Chimie). Non-limiting examples of modified nonionic guar gums include Jaguar HP8, HP60, HP120, DC 293 and HP 105 (Meyhall/Rhodia Chimie); Galactasol 4H4FD2 (Aqualon).

Among these gums, mention will be made of scleroglucans such as, for example, Actigum CS from Sanofi Bio Industries; Amigel from Alban Muller International, and also the glyoxal-treated scleroglucans described in FR2633940); xanthan gums, for instance Keltrol®, Keltrol® T, Keltrol® Tf, Keltrol® Bt, Keltrol® Rd, Keltrol® Cg (Nutrasweet Kelco), Rhodicare® S and Rhodicare® H (Rhodia Chimie); starch derivatives, for instance Primogel® (Avebe); hydroxyethylcelluloses such as Cellosize® QP3L, QP4400H, QP30000H, HEC30000A and Polymer PCG10 (Amerchol), Natrosol 250HHR®, 250MR, 250M, 250HHXR, 250HHX, 250HR, HX (Hercules) and Tylose® H1000 (Hoechst); hydroxypropylcelluloses, for instance Klucel® EF, H, LHF, MF and G (Aqualon); carboxymethylcelluloses, for instance Blanose® 7M8/SF, refined 7M, 7LF, 7MF, 9M31F, 12M31XP, 12M31P, 9M31XF, 7H, 7M31, 7H3SXF (Aqualon), Aquasorb® A500 (Hercules), Ambergum® 1221 (Hercules), Cellogen® HP810A, HP6HS9 (Montello) and Primellose® (Avebe).

Associative polymers may be chosen from, by way of example only, those described in WO11076792, incorporated by reference herein, including but not limited to associative polyurethanes which are cationic or nonionic, associative cellulose derivatives which are cationic or nonionic, associative vinyllactams, associative unsaturated polyacids, associative aminoplast ethers, and associative polymers or copolymers comprising at least one monomer comprising ethylenic unsaturation, and comprising a sulpho group.

An example of an associative polyurethanes is methacrylic acid/methyl acrylate/ethoxylated (40 EO) behenyl alcohol dimethyl(meta-isopropenyl)benzyl isocyanate terpolymer as a 25 percent aqueous dispersion, known by the trade name, Viscophobe® DB 1000 and commercially available from Amerchol.

More particularly, preference is given to the use of a polyether polyurethane capable of being obtained by polycondensation of at least three compounds comprising (i) at least one polyethylene glycol comprising from 150 to 180 mol of ethylene oxide, (ii) stearyl alcohol or decyl alcohol and (iii) at least one diisocyanate.

Such polyether polyurethanes are sold in particular by Rohm and Haas under the names ACULYN 46® and ACULYN 44® [ACULYN 46® is a polycondensate of polyethylene glycol comprising 150 or 180 mol of ethylene oxide, of stearyl alcohol and of methylenebis(4-cyclohexyl isocyanate) (SMDI), at 15 percent by weight in a matrix of maltodextrin (4%) and of water (81% ACULYN 44® is a polycondensate of polyethylene glycol comprising 150 or 180 mol of ethylene oxide, of decyl alcohol and of methylenebis(4-cyclohexyl isocyanate) (SMDI), at 35 percent) by weight in a mixture of propylene glycol (39%) and of water (26%)].

Associative celluloses may also be used, such as quaternized cationic celluloses and quaternized cationic hydroxyethylcelluloses modified by groups comprising at least one hydrophobic chain, such as alkyl, arylalkyl or alkylaryl groups comprising at least 8 carbon atoms, or blends thereof.

The alkyl radicals carried by the above quaternized celluloses or hydroxyethylcelluloses may, in various embodiments, comprise from 8 to 30 carbon atoms. The aryl radicals may, for example, denote the phenyl, benzyl, naphthyl or anthryl groups.

There may be indicated, as examples, of quaternized alkylhydroxy-ethylcelluloses comprising a C8-C30 hydrophobic chain, the products Quatrisoft LM 200®, Quatrisoft LM-X 529-18-A®, Quatrisoft LM-X 529-18B® ($C_{12}$ alkyl) and Quatrisoft LM-X 529-8® (Ci8 alkyl) sold by Amerchol and the products Crodacel QM®, Crodacel QL® (C12 alkyl) and Crodacel QS® ($Ci_8$ alkyl) sold by Croda.

Nonionic cellulose derivatives may be chosen, such as hydroxyethylcelluloses modified by groups comprising at least one hydrophobic chain, such as alkyl, arylalkyl or alkylaryl groups, or their blends, and in which the alkyl groups are, for example, $C_8$-$C_{22}$ alkyl groups, such as the product Natrosol Plus Grade 330 CS® ($C_{16}$ alkyls) sold by Aqualon or the product Bermocoll EHM 100® sold by Berol Nobel.

Cellulose derivatives modified by alkylphenyl polyalkylene glycol ether groups may also be chosen, such as the product Amercell Polymer HM-1500® sold by Amerchol.

As regards the associative polyvinyllactams, mention may be made, by way of example only, of the polymers described in particular in FR 0101106. The said polymers are, for example, cationic polymers. Use may in particular be made, as poly(vinyllactam) polymers, of vinylpyrrolidone/dimethylaminopropyl-methacrylamide/dodecyldimethylmethacrylamidopropylammonium tosylate terpolymers, vinylpyrrolidone/dimethylaminopropylmethacrylamide/cocoyldimethylmethacrylamidopropylammonium tosylate terpolymers or vinylpyrrolidone/dimethylaminopropylmethacrylamide/lauryldimethylmethacrylamidopropylammonium tosylate or chloride terpolymers. The vinylpyrrolidone/dimethylaminopropylmethacrylamide/lauryldimethylmethacrylamidopropylammonium chloride terpolymer is provided at 20 percent in water by ISP under the name Styleze® W20.

Associative polyvinyllactam derivatives can also be nonionic copolymers of vinylpyrrolidone and of hydrophobic monomers comprising a hydrophobic chain, for example, the products Antaron V216® or Ganex V2 16® (vinylpyrrolidone/hexadecene copolymer) sold by ISP, or the products Antaron V220® or Ganex V220® (vinylpyrrolidone/eicosene copolymer) sold by ISP.

Examples of associative polymers comprising an aminoplast ether backbone are the products Pure-Thix® L (PEG-1 80/Octoxynol-40/TMMG Copolymer), Pure-Thix M® (PEG-1 80/Laureth-50/TMMG Copolymer), Pure-Thix® HH (Polyether-1); Pure-Thix TX-1442® (PEG-1 8/dodoxynol-5/PEG-25 tristyrylphenol/tetramethoxymethyl-glycoluril copolymer), which are provided by Sud-Chemie.

Associative polymers may also be chosen from water-soluble thickening polymers. In various exemplary embodiments, the at least one rheology-modifying agent may be chosen from thickening polymers comprising at least one fatty chain, such as described in U.S. Pat. No. 7,771,492; thickening polymers chosen from (i) copolymers resulting from the polymerization of at least one monomer (a) chosen from carboxylic acids possessing α,β-ethylinic unsaturation or their esters with at least one monomer (b) possessing ethylinic unsaturation comprising a hydrophobic group, (ii) polymers comprising at least one monomer possessing a sulpho group, and mixtures thereof, such as described in US20110088711; rheological agents such as crystalline and semi-crystalline polymers, esters of dextrin and a fatty acid, modified hydrophobic polysaccharides, crystalline olefin copolymers, crystalline polycondensates, lipophilic miners structure-forming agents, lipophilic polyamide polymers, lipophilic polyureas and polyurethanes, silicone polymers, organic gelling agents, block copolymers, silicone elastomers, cholesteric liquid crystal agents, waxes, and mixtures thereof, such as described in US20110200543; and non-associative thickening polymers, such as described in U.S. Pat. No. 7,250,064, the disclosures of which are all incorporated by reference herein.

In certain exemplary embodiments, the rheology-modifying agents are chosen from cellulose derivatives, polysaccharides, gums, clays, fumed silica, acrylates, polyacrylamides, crosslinked polyacrylic acids, crosslinked acrylamide polymers and copolymers, crosslinked methacryloyloxyethltrimethyl-ammonium chloride homopolymers, and associative polymers. Said rheology-modifying agents may include, in particular embodiments, xanthan gum, gum arabic, ghatti gum, karaya gum, gum tragacanth, carrageenan gum, agar gum, carob gum, pectins, alginates, starches, hydroxy($C_1$-$C_6$)alkylcelluloses, carboxy($C_1$-$C_6$)alkylcelluloses, and mixtures thereof.

In various embodiments, the at least one rheology-modifying agent may be present in an amount ranging from about 0.1% to about 40% by weight, such as from about 0.1% to about 30% by weight, from about 0.5% to about 30% by weight, from about 0.5% to about 25% by weight, or from about 1% to about 20% by weight, based on the total weight of the composition. In at least one exemplary embodiment, the at least one rheology-modifying agent may be present in an amount of at least about 1% by weight, based on the total weight of the composition.

Chelants

Exemplary chelants that may be useful in various embodiments according to the disclosure include, but are not limited to, diamine-N,N'-dipolyacid, monoamine monoamide-N,N'-dipolyacid, and N,N'-bis(2-hydroxybenzyl)-ethylenediamine-N,N'-diacetic acid chelants, carboxylic acids (e.g. aminocarboxylic acids), phosphonic acids (e.g. aminophosphonic acids), and polyphosphoric acids (e.g., linear polyphosphoric acids), and salts and derivatives thereof. Chelants are well known in the art, and a non-exhaustive list thereof can be found in A E Martell and R M Smith, Critical Stability Constants, Vol. 1, Plenum Press, New York and London (1974), and A E Martell and R D Hancock, Metal Complexes in Aqueous Solution, Plenum Press, New York and London (1996), the disclosures of which are incorporated herein by reference.

As used herein with regard to chelants, the phrase "salts and derivatives thereof" is intended to mean all salts and derivatives comprising the same functional structure as the chelant they are referring to, and that have similar or better chelating properties. These terms include, for example, alkali metal, alkaline earth, ammonium, substituted ammonium salts (e.g monoethanolammonium, diethanolammonium, triethanolammonium), esters of chelants having an acidic moiety and mixtures thereof, in particular all sodium, potassium or ammonium salts. The term "derivatives" also includes "chelating surfactant" compounds (i.e. chelants modified to bear a surfactant moiety while keeping the same chelating functionality). The term "derivatives" also includes large molecules comprising one or more chelating groups having the same functional structure as the parent chelants, such as, for example, polymeric ethylenediamine-N,N'-disuccinic acid (EDDS).

By way of example, aminocarboxylic acid chelants may be chosen from chelants having at least one carboxylic acid moiety (—COOH) and at least one nitrogen atom. Non-limiting examples of aminocarboxylic acid chelants suitable for use according to various embodiments of the disclosure include diethylenetriamine pentaacetic acid (DTPA), ethylenediamine-N,N'-disuccinic acid (EDDS), ethylenediamine diglutaric acid (EDGA), 2-hydroxypropylenediamine disuccinic acid (HPDS), glycinamide-N,N'-disuccinic acid (GADS), ethylenediamine-N—N'-diglutaric acid (EDDG), 2-hydroxypropylenediamine-N—N'-disuccinic acid (HPDDS), ethylenediaminetetraacetic acid (EDTA), ethylenedicysteic acid (EDC), EDDHA (ethylenediamine-N—N'-bis(ortho-hydroxyphenyl acetic acid)), diaminoalkyldi-(sulfosuccinic acids) (DDS), N,N'-bis(2-hydroxybenzyl) ethylenediamine-N,N'-diacetic acid (HBED), and salts and derivatives thereof.

Other suitable non-limiting aminocarboxylic type chelants are iminodiacetic acid derivatives, such as N-2-hydroxyethyl N,N diacetic acid or glyceryl imino diacetic acid, iminodiacetic acid-N-2-hydroxypropyl sulfonic acid and aspartic acid, N-carboxymethyl N-2-hydroxypropyl-3-sulfonic acid, beta-alanine-N,N'-diacetic acid, aspartic acid-N, N'-diacetic acid, aspartic acid-N-monoacetic acid, and iminodisuccinic acid chelants, ethanoldiglycine acid, and salts and derivatives thereof. Dipicolinic acid and 2-phosphonobutane-1,2,4-tricarboxylic acid are also suitable.

In various exemplary embodiments, aminophosphonic acid type chelants, salts thereof, derivatives thereof and mixtures thereof, may be chosen. Aminophosphonic acid-type chelants include, for example, chelants comprising an amino-phosphonic acid moiety (—$PO_3H_2$) or its derivative —$PO_3R2$, wherein R2 is a $C_1$ to $C_6$ alkyl or aryl radical. Non-limiting aminophosphonic acid-type chelants may be chosen from aminotri-(1-ethylphosphonic acid), ethylenediaminetetra-(1-ethylphosphonic acid), aminotri-(1-propylphosphonic acid), and aminotri-(isopropylphosphonic acid). In further exemplary embodiments, the aminophosphonic acid type chelant may be chosen from aminotri(methylenephosphonic acid), ethylene-diamine-tetra-(methylenephosphonic acid) (EDTMP), diethylene-triamine-penta-(methylenephosphonic acid) (DTPMP), or mixtures thereof.

Examples of other chelants suitable for use according to embodiments of the disclosure include, but are not limited to, quercetin polyethyleneimines, polyphosphoric acid chelants, editronic acid, methylglycine diacetic acid, N-(2-hydroxyethyl)iminodiacetic acid, iminodisuccinnic acid, N,N-Dicarboxymethyl-L-glutamic acid and N-lauroyl-N,N',N-ethylenediamine diacetic acid.

In various exemplary embodiments, the compositions comprise one or more chelants chosen from diethylenetriamine pentaacetic acid (DTPA), ethylenediamine-N,N'-disuccinic acid (EDDS), ethylenediamine-N,N'-diglutaric acid (EDDG), 2-hydroxypropylenediamine-N,N'-disuccinic acid (HPDDS), glycinamide-N,N'-disuccinic acid (GADS), ethylenediamine-N—N'-bis(ortho-hydroxyphenyl acetic acid) (EDDHA), diethylene-triamine-penta-(methylenephosphonic acid) (DTPMP), salts thereof, derivatives thereof, or mixtures thereof.

In at least one exemplary embodiment, the chelant may be chosen from ethylenediamine-N,N'-disuccinic acid (EDDS).

In at least one further exemplary embodiment, the chelant may be chosen from etidronic acid. In various embodiments, one or both of these chelants may be chosen for their efficiency, safety, and/or biodegradability.

In various embodiments, the at least one chelant may be present in an amount sufficient to reduce the amount of metals available to interact with formulation components, such as oxidizing agents. By way of example, the at least one chelant may be present in an amount up to about 10% by weight, such as an amount ranging from about 0.01% to about 5% by weight, about 0.25% to about 3% by weight, or about 0.5% to about 1% by weight, based on the total weight of the composition. In at least one embodiment, the chelant may be present in an amount of at least 0.25%, such as at least 0.5%. In a further exemplary embodiment, the composition comprises from about 0.1% to about 5% by weight of diethylene-triamine-penta-(methylenephosphonic acid), and from about 0.1% to about 5% by weight of ethylene-diamine-N,N'-disuccinic acid.

Fatty Substances

Exemplary fatty substances that may be used in various embodiments of the disclosure include, but are not limited to, organic compounds that are insoluble in water at normal temperature (25° C. and at atmospheric pressure (760 mmHg) (solubility below 5% and such as below 1% and further such as below 0.1%). Fatty substances have in their structure a chain of at least two siloxane groups, or at least one hydrocarbon chain having at least 6 carbon atoms. Moreover, fatty substances are generally soluble in organic solvents in the same conditions of temperature and pressure, for example in chloroform, ethanol, benzene or decamethylcyclopentasiloxane.

Fatty substances may be, for example, chosen from lower alkanes, fatty alcohols, esters of fatty acid, esters of fatty alcohol, oils such as mineral, vegetable, animal and synthetic non-silicone oils, non-silicone waxes and silicones.

In some embodiments, the alcohols and esters have at least one linear or branched, saturated or unsaturated hydrocarbon group, comprising 6 to 30 carbon atoms, optionally substituted, for example, with at least one hydroxyl group (for example 1 to 4). If they are unsaturated, these compounds can have one to three, conjugated or unconjugated, carbon-carbon double bonds.

With regard to the lower alkanes, in some embodiments, these have from 6 to 16 carbon atoms and are linear or branched, optionally cyclic. As examples, alkanes can be chosen from hexane and dodecane, isoparaffins such as isohexadecane and isodecane.

Examples of non-silicone oils that may be used in various embodiments of the disclosure, include, but are not limited to, hydrocarbon oils of animal origin, such as perhydrosqualene; hydrocarbon oils of vegetable origin, such as liquid triglycerides of fatty acids having from 6 to 30 carbon atoms such as triglycerides of heptanoic or octanoic acids, or for example sunflower oil, maize oil, soya oil, cucurbit oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names MIGLYOL® 810, 812 and 818 by the company Dynamit Nobel, jojoba oil, shea butter oil; hydrocarbons with more than 16 carbon atoms, linear or branched, of mineral or synthetic origin, such as paraffin oils, petroleum jelly, liquid paraffin, polydecenes, hydrogenated polyisobutene such as Parleam® fluorinated, partially hydrocarbon oils; as fluorinated oils, non-limiting examples include perfluoromethylcyclopentane and perfluoro-1,3-dimethylcyclohexane, sold under the names "FLUTEC® PC1" and "FLUTEC® PC3" by the company BNFL Fluorochemicals; perfluoro-1,2-dimethylcyclobutane; perfluoroalkanes such as dodecafluoropentane and tetradecafluorohexane, sold under the names "PF 5050®" and "PF 5060®" by the 3M Company, or bromoperfluorooctyl sold under the name "FORALKYL®" by the company Atochem; nonafluoromethoxybutane and nonafluoroethoxyisobutane; derivatives of perfluoromorpholine, such as 4-trifluoromethyl perfluoromorpholine sold under the name "PF 5052®" by the 3M Company.

The fatty alcohols that may be chosen as the at least one fatty substance include, but are not limited to, non-alkoxylated, saturated or unsaturated, linear or branched, and have from 6 to 30 carbon atoms and more particularly from 8 to 30 carbon atoms. For example, cetyl alcohol, stearyl alcohol and their mixture (cetylstearyl alcohol), octyldodecanol, 2-butyloctanol, 2-hexyldecanol, 2-undecylpentadecanol, oleic alcohol or linoleic alcohol may be chosen.

The exemplary non-silicone wax or waxes that can be used may be chosen from carnauba wax, candelilla wax, Alfa wax, paraffin wax, ozokerite, vegetable waxes such as olive wax, rice wax, hydrogenated jojoba wax, or absolute waxes of flowers, such as the essential wax of blackcurrant flower sold by the company BERTIN (France), animal waxes such as beeswaxes, or modified beeswaxes (cerabellina). Further waxes or waxy raw materials usable according to the disclosure are, for example, marine waxes such as that sold by the company SOPHIM under reference M82, waxes of polyethylene or of polyolefins in general.

The exemplary fatty acid esters are the esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total number of carbons of the esters being, for example, greater than or equal to 10.

Among the monoesters, non-limiting mentions can be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methyl acetyl ricinoleate; myristyl stearate; octyl isononanoate; 2-ethylhexyl isononate; octyl palmitate; octyl pelargonate; octyl stearate; octyldodecyl erucate; oleyl erucate; ethyl and isopropyl palmitates, ethyl-2-hexyl palmitate, 2-octyldecyl palmitate, alkyl myristates such as isopropyl, butyl, cetyl, 2-octyldodecyl, mirystyl, stearyl myristate, hexyl stearate, butyl stearate, isobutyl stearate; dioctyl malate, hexyl laurate, and 2-hexyldecyl laurate.

Further non-limiting examples of esters include esters of $C_4$-$C_{22}$ di- or tricarboxylic acids and of $C_1$-$C_{22}$ alcohols and the esters of mono-, di- or tricarboxylic acids and of $C_2$-$C_{26}$ di-, tri-, tetra- or pentahydroxy alcohols.

Even further non-limiting examples of esters include: diethyl sebacate; diisopropyl sebacate; diisopropyl adipate; di-n-propyl adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate, tridecyl erucate; triisopropyl citrate; triisostearyl citrate; glyceryl trilactate; glyceryl trioctanoate; trioctyldodecyl citrate; trioleyl citrate, propylene glycol dioctanoate;

neopentyl glycol diheptanoate; diethylene glycol diisanonate; and polyethylene glycol distearates.

Among the esters mentioned above, exemplary esters include ethyl, isopropyl, myristyl, cetyl, stearyl palmitates, ethyl-2-hexyl palmitate, 2-octyldecyl palmitate, alkyl myristates such as isopropyl, butyl, cetyl, 2-octyldodecyl myristate, hexyl stearate, butyl stearate, isobutyl stearate; dioctyl malate, hexyl laurate, 2-hexyldecyl laurate and isononyl isononanate, cetyl octanoate.

The composition can also comprise, as fatty ester, esters and di-esters of sugars of $C_6$-$C_{30}$, such as $C_{12}$-$C_{22}$ fatty acids. "Sugar" as used here means oxygen-containing hydrocarbon compounds that possess several alcohol functions, with or without aldehyde or ketone functions, and having at least 4 carbon atoms. These sugars can be monosaccharides, oligosaccharides or polysaccharides.

As suitable sugars, non-limiting examples include sucrose, glucose, galactose, ribose, fucose, maltose, fructose, mannose, arabinose, xylose, lactose, and their derivatives, for example alkylated, such as methylated derivatives such as methylglucose.

The esters of sugars and of fatty acids may be, for example, chosen from the esters or mixtures of esters of sugars described previously and of linear or branched, saturated or unsaturated $C_6$-$C_{30}$, such as $C_{12}$-$C_{22}$ fatty acids. If they are unsaturated, these compounds can have one to three, conjugated or unconjugated, carbon-carbon double bonds.

The esters according to at least one embodiment can also be chosen from mono-, di-, tri- and tetra-esters, polyesters and mixtures thereof.

These esters can be, for example, oleate, laurate, palmitate, myristate, behenate, cocoate, stearate, linoleate, linolenate, caprate, arachidonates, or mixtures thereof such as the oleo-palmitate, oleo-stearate, palmito-stearate mixed esters.

For example, the mono- and di-esters can be used, and such as the mono- or di-oleate, stearate, behenate, oleopalmitate, linoleate, linolenate, oleostearate, of sucrose, of glucose or of methylglucose.

One non-limiting example useful in various embodiments includes the product sold under the name GLUCATE® DO by the company Amerchol, which is a dioleate of methylglucose.

Exemplary esters or mixtures of esters of sugar of fatty acid include: the products sold under the names F160, F140, F110, F90, F70, SL40 by the company Crodesta, denoting respectively the palmito-stearates of sucrose formed from 73% of monoester and 27% of di- and tri-ester, from 61% of monoester and 39% of di-, tri-, and tetra-ester, from 52% of monoester and 48% of di-, tri-, and tetra-ester, from 45% of monoester and 55% of di-, tri-, and tetra-ester, from 39% of monoester and 61% of di-, tri-, and tetra-ester, and the mono-laurate of sucrose; the products sold under the name Ryoto Sugar Esters for example with the reference B370 and corresponding to the behenate of sucrose formed from 20% of monoester and 80% of di-triester-polyester; sucrose mono-di-palmito-stearate marketed by the company Goldschmidt under the name TEGOSOFT® PSE.

Silicones usable in the composition of the present disclosure include but are not limited to volatile or non-volatile, cyclic, linear or branched silicones, modified or not with organic groups, having a viscosity from $5\times10^{-6}$ to 2.5 m²/s at 25° C., such as from $1\times10^{-5}$ to 1 m²/s.

The silicones usable according to the disclosure can be in the form of oils, waxes, resins or gums.

In some embodiments, the silicone may be chosen from the polydialkylsiloxanes, such as the polydimethylsiloxanes (PDMS), and the organomodified polysiloxanes having at least one functional group chosen from the poly(alkoxylated) groups, the amine groups and the alkoxy groups.

The organopolysiloxanes are defined in more detail in the work of Walter NOLL "Chemistry and Technology of Silicones" (1968), Academic Press. They can be volatile or non-volatile.

When they are volatile, the silicones are, for example, chosen from those with a boiling point between 60° C. and 260° C. By way of example, the silicones may be chosen from cyclic polydialkylsiloxanes having from 3 to 7, such as from 4 to 5, silicon atoms. Various exemplary silicones may be the octamethylcyclotetrasiloxane marketed under the name VOLATILE SILICONE® 7207 by UNION CARBIDE or SILBIONE® 70045 V2 by RHODIA, the decamethylcyclopentasiloxane marketed under the name VOLATILE SILICONE® 7158 by UNION CARBIDE, and SILBIONE® 70045 V5 by RHODIA, and mixtures thereof.

Non-limiting examples may also include the cyclocopolymers of the dimethylsiloxanes/methylalkylsiloxane type, such as SILICONE VOLATILE® FZ 3109 marketed by the company UNION CARBIDE, of the following formula (II):

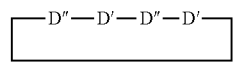

with D":

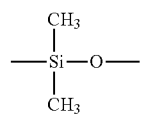

with D':

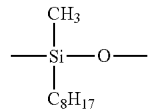

Further non-limiting examples may include mixtures of cyclic polydialkylsiloxanes with organic compounds derived from silicon, such as the mixture of octamethylcyclotetrasiloxane and tetratrimethylsilylpentaerythritol (50/50) and the mixture of octamethylcyclotetrasiloxane and oxy-1,1'-(hexa-2,2,2',2',3,3'-trimethylsilyloxy)bis-neopentane.

Other suitable volatile silicones include the linear volatile polydialkylsiloxanes having 2 to 9 silicon atoms and with a viscosity less than or equal to $5\times10^{-6}$ m²/s at 25° C. One non-limiting example is decamethyltetrasiloxane, marketed under the name "SH 200" by the company TORAY SILICONE. Silicones included in this class are also described in the article published in Cosmetics and Toiletries, Vol. 91, January 76, p. 27-32-TODD BYERS "Volatile Silicone fluids for cosmetics," which is incorporated by reference herein.

Even further non-limiting mentions can be made of non-volatile polydialkylsiloxanes, gums and resins of polydialkylsiloxanes, polyorganosiloxanes modified with the aforementioned organofunctional groups, and mixtures thereof.

These silicones may be, for example, chosen from the polydialkylsiloxanes, such as the polydimethylsiloxanes with trimethylsilyl end groups. The viscosity of the silicones is measured at 25° C. according to Standard Test Method for Kinematic Viscosity of Transparent and Opaque Liquids (and Calculation of Dynamic Viscosity).

Among these polydialkylsiloxanes, mention can be made of, non-exhaustively, the following commercial products: the SILBIONE® oils of series 47 and 70 047 or the MIRASIL® oils marketed by RHODIA, for example the oil 70 047 V 500,000; the oils of the MIRASIL® series marketed by the company RHODIA; the oils of the 200 series from the company DOW CORNING such as DC200, with a viscosity of 60,000 mm$^2$/s; the VISCASIL® oils from GENERAL ELECTRIC and certain oils of the SF series (SF 96, SF 18) from GENERAL ELECTRIC.

Non-limiting mention can also be made of the polydimethylsiloxanes with dimethylsilanol end groups known under the name of dimethiconol (CTFA), such as the oils of the 48 series from the company RHODIA.

In this class of polydialkylsiloxanes, non-limiting mentions can be made of the products marketed under the names "ABIL WAX® 9800 and 9801" by the company GOLDSCHMIDT, which are polydialkyl ($C_1$-$C_{20}$) siloxanes.

The silicone gums usable according to the disclosure are, for example, polydialkylsiloxanes, such as polydimethylsiloxanes with high number-average molecular weights between 200,000 and 1,000,000 used alone or mixed in a solvent. This solvent can be chosen from the volatile silicones, the polydimethylsiloxane (PDMS) oils, the polyphenylmethylsiloxane (PPMS) oils, the isoparaffins, the polyisobutylenes, methylene chloride, pentane, dodecane, tridecane and mixtures thereof.

Products useful according to various embodiments of the disclosure include, for example, mixtures such as those formed from a chain end hydroxylated polydimethylsiloxane, or dimethiconol (CTFA) and a cyclic polydimethylsiloxane also called cyclomethicone (CTFA), such as the product Q2 1401 marketed by the company DOW CORNING; mixtures of a polydimethylsiloxane gum and a cyclic silicone such as the product SF 1214 Silicone Fluid from the company GENERAL ELECTRIC, said product being a gum SF 30 corresponding to a dimethicone, having a number-average molecular weight of 500,000, dissolved in the oil SF 1202 Silicone Fluid corresponding to decamethylcyclopentasiloxane; mixtures of two PDMS of different viscosities, for example, of a PDMS gum and a PDMS oil, such as the product SF 1236 from the company GENERAL ELECTRIC. The product SF 1236 is a mixture of a gum SE 30 as defined above having a viscosity of 20 m$^2$/s and an oil SF 96 with a viscosity of 5×10$^{-6}$ m$^2$/s. This product, for example, has 15% of gum SE 30 and 85% of oil SF 96.

The organopolysiloxane resins usable according to the disclosure include, but are not limited to, crosslinked siloxane systems containing the units: $R_2SiO_{2/2}$, $R_3SiO_{1/2}$, $RSiO_{3/2}$ and $SiO_{4/2}$, wherein R represents an alkyl having from 1 to 16 carbon atoms. For example, R may denote a $C_1$-$C_4$ lower alkyl group, such as methyl.

Among these resins, non-limiting mention can be made of the product marketed under the name "DOW CORNING® 593" or those marketed under the names "SILICONE FLUID SS 4230 and SS 4267" by the company GENERAL ELECTRIC, which are silicones of dimethyl/trimethyl siloxane structure.

Non-limiting mention can also be made of the resins of the trimethylsiloxysilicate type, such as those marketed under the names X22-4914, X21-5034 and X21-5037 by the company SHIN-ETSU.

The organomodified silicones usable according to the disclosure include but are not limited to silicones as defined previously, having in their structure at least one organofunctional group fixed by a hydrocarbon group.

In addition to the silicones described above, the organomodified silicones can be polydiaryl siloxanes, such as polydiphenylsiloxanes, and polyalkylarylsiloxanes functionalized by the aforementioned organofunctional groups.

The polyalkarylsiloxanes are, for example, chosen from the polydimethyl/methylphenylsiloxanes, the polydimethyl/diphenylsiloxanes, linear and/or branched, with viscosity ranging from $1 \times 10^{-5}$ to $5 \times 10^2$ m$^2$/s at 25° C.

Among these polyalkarylsiloxanes, non-limiting mention can be made of the products marketed under the following names: the SILBIONE® oils of series 70 641 from RHODIA; the oils of the series RHODORSIL® 70 633 and 763 from RHODIA; the oil DOW CORNING® 556 COSMETIC GRADE FLUID from DOW CORNING; the silicones of the PK series from BAYER such as the product PK20; the silicones of the series PN, PH from BAYER such as the products PN1000 and PH1000; certain oils of the SF series from GENERAL ELECTRIC such as SF 1023, SF 1154, SF 1250, SF 1265.

Among the organomodified silicones, non-limiting mention can be made of the polyorganosiloxanes having: polyoxyethylene and/or polyoxypropylene groups optionally with $C_6$-$C_{24}$ alkyl groups such as the products called dimethicone copolyol marketed by the company DOW CORNING under the name DC 1248 or the oils SILWET® L 722, L 7500, L 77, L 711 from the company UNION CARBIDE and the alkyl ($C_{12}$)-methicone copolyol marketed by the company DOW CORNING under the name Q2 5200; substituted or unsubstituted amine groups such as the products marketed under the name GP 4 Silicone Fluid and GP 7100 by the company GENESEE or the products marketed under the names Q2 8220 and DOW CORNING® 929 or 939 by the company DOW CORNING. The substituted amine groups are, for example, $C_1$-$C_4$ aminoalkyl groups; alkoxylated groups, such as the product marketed under the name "SILICONE COPOLYMER F-755" by SWS SILICONES and ABIL WAX® 2428, 2434 and 2440 by the company GOLDSCHMIDT.

In various exemplary embodiments, the at least one fatty substance is neither alkoxylated, nor glycerolated. For example, the at least one fatty substance may be chosen from compounds that are liquid or pasty at room temperature and atmospheric pressure. By way of example, the at least one fatty substance may be a compound that is liquid at a temperature of 25° C., and atmospheric pressure.

Exemplary fatty substances may be, for example, chosen from the lower alkanes, fatty alcohols, esters of fatty acid, esters of fatty alcohol, and oils such as non-silicone mineral, vegetable and synthetic oils, the silicones.

According to at least one embodiment, the at least one fatty substance is chosen from liquid paraffin, polydecenes, liquid esters of fatty acids and of fatty alcohols, and mixtures thereof, for example, the at least one fatty substance of the composition according to the disclosure can be non-silicone.

In some embodiments, the at least one fatty substance is chosen from alkanes, hydrocarbons and silicones.

In further exemplary embodiments, the at least one fatty substance may be chosen from fatty acids. By way of example only, fatty acids having from about 6 to about 40 carbon atoms may be chosen, including but not limited to Arachidic Acid, Arachidonic Acid, Beeswax Acid, Capric Acid, Caproic Acid, Caprylic Acid, Coconut Acid, Isostearic Acid, Lauric Acid, Linoleic Acid, Linolenic Acid, Myristic Acid, Oleic Acid, Olive Acid, Palmitic Acid, Rapeseed Acid, Stearic Acid, Tallow Acid, Undecanoic Acid, Undecylenic Acid, Wheat Germ Acid.

In various exemplary embodiments, fatty acids having from about 6 to about 40 carbon atoms are chosen from Capric Acid, Caprylic Acid, Lauric Acid, Oleic Acid, Isostearic Acid, and Stearic Acid.

In various embodiments, the at least one fatty substance may be present in an amount of at least about 10% by weight, such as from about 10% to about 80% by weight, such as from about 15% to about 65% by weight, or from about 20% to about 55% by weight, based on the total weight of the composition.

Ceramides

Ceramide compounds that may be useful according to various embodiments include ceramides, glycoceramides, pseudoceramides, and mixtures thereof. The ceramides which may be used include, but are not limited to, those described by DOWNING in Arch. Dermatol, Vol. 123, 1381-1384 (1987), DOWNING in Journal of Lipid Research, Vol. 35, page 2060 (1994), or those described in French patent FR 2673179, all of which are incorporated by reference herein.

Further exemplary ceramides that may be used according to various embodiments of the disclosure include, but are not limited to, compounds of the general formula (III):

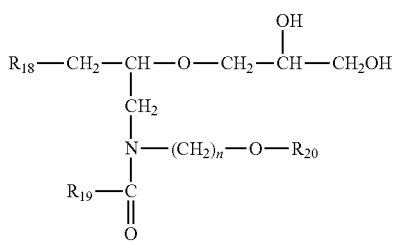

wherein, in formula (III):
$R_{18}$ and $R_{19}$ are, independently, chosen from alkyl- or alkenyl groups with 10 to 22 carbon atoms,
$R_{20}$ is chosen from methyl, ethyl, n-propyl or isopropyl groups, and
n is a number ranging from 1 to 6, such as, for example, 2 or 3.

In further embodiments, ceramide compounds may be chosen from compounds of formula (IV), as described in US20050191251 and US20090282623, both of which are incorporated by reference herein:

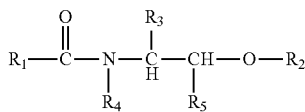

wherein, in formula (IV):
$R_1$ is chosen from either a saturated or unsaturated, linear or branched $C_1$-$C_{50}$, e.g. $C_5$-$C_{50}$, hydrocarbon radical, it being possible for this radical to be substituted with one or more hydroxyl groups optionally esterified with an acid $R_7COOH$, $R_7$ being an optionally mono- or polyhydroxylated, linear or branched, saturated or unsaturated $C_1$-$C_{35}$ hydrocarbon radical, it being possible for the hydroxyl(s) of the radical $R_7$ to be esterified with an optionally mono- or polyhydroxylated, linear or branched, saturated or unsaturated $C_1$-$C_{35}$ fatty acid, or a radical R"—(NR—CO)—R', R being chosen from a hydrogen atom or a mono- or polyhydroxylated, e.g. monohydroxylated, $C_1$-$C_{20}$ hydrocarbon radical, R' and R" chosen from, independently, hydrocarbon radicals of which the sum of the carbon atoms is between 9 and 30, R' being a divalent radical, or a radical $R_8$—O—CO—$(CH_2)$p, $R_8$ denoting a $C_1$-$C_{20}$ hydrocarbon radical, p being an integer varying from 1 to 12;

$R_2$ being chosen from a hydrogen atom, a saccharide-type radical, in particular a (glycosyl)n, (galactosyl)m and sulphogalactosyl radical, a sulphate or phosphate residue, a phosphorylethylamine radical and a phosphorylethylammonium radical, in which n is an integer varying from 1 to 4 and m is an integer varying from 1 to 8;

$R_3$ chosen from a hydrogen atom or a hydroxylated or nonhydroxylated, saturated or unsaturated, $C_1$-$C_{33}$ hydrocarbon radical, it being possible for the hydroxyl(s) to be esterified with an inorganic acid or an acid $R_7COOH$, $R_7$ having the same meanings as above, and it being possible for the hydroxyl(s) to be etherified with a (glycosyl)n, (galactosyl)m, sulphogalactosyl, phosphorylethylamine or phosphorylethylammonium radical, it being also possible for $R_3$ to be substituted with one or more $C_1$-$C_{14}$ alkyl radicals;

$R_4$ being chosen from a hydrogen atom, a methyl or ethyl radical, an optionally hydroxylated, linear or branched, saturated or unsaturated $C_3$-$C_{50}$ hydrocarbon radical or a radical —$CH_2$—CHOH—$CH_2$—O—$R_6$ in which $R_6$ denotes a $C_{10}$-$C_{26}$ hydrocarbon radical or a radical $R_8$—O—CO—$(CH_2)$p, $R_8$ chosen from a $C_1$-$C_{20}$ hydrocarbon radical, p being an integer varying from 1 to 12; and $R_5$ denotes a hydrogen atom or an optionally mono- or polyhydroxylated, linear or branched, saturated or unsaturated $C_1$-$C_{30}$ hydrocarbon radical, it being possible for the hydroxyl(s) to be etherified with a (glycosyl)n, (galactosyl)m, sulphogalactosyl, phosphorylethylamine or phosphorylethylammonium radical, with the proviso that when $R_3$ and $R_5$ denote hydrogen or when $R_3$ denotes hydrogen and $R_5$ denotes methyl, then $R_4$ does not denote a hydrogen atom, or a methyl or ethyl radical.

By way of example, ceramides of formula (IV) may be chosen from those wherein $R_1$ is an optionally hydroxylated, saturated or unsaturated alkyl radical derived from $C_{14}$-$C_{22}$ fatty acids; $R_2$ is a hydrogen atom; and $R_3$ is an optionally hydroxylated, saturated, linear $C_{11}$-$C_{17}$, e.g. $C_{13}$-$C_{15}$ radical.

In yet further embodiments, ceramide compounds useful according to the disclosure may be chosen from compounds of the general formula (V):

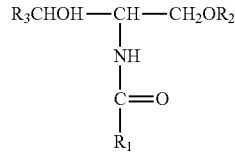

wherein, in formula (V):
- $R_1$ is chosen from a linear or branched, saturated or unsaturated alkyl group, derived from $C_{14}$-$C_{30}$ fatty acids, it being possible for this group to be substituted with a hydroxyl group in the alpha-position, or a hydroxyl group in the omega-position esterified with a saturated or unsaturated $C_{16}$-$C_{30}$ fatty acid;
- $R_2$ is chosen from a hydrogen atom or a (glycosyl)$_n$, (galactosyl)$_m$ or sulphogalactosyl group, in which n is an integer ranging from 1 to 4 and m is an integer ranging from 1 to 8; and
- $R_3$ is chosen from a $C_5$-$C_{26}$ hydrocarbon-based group, saturated or unsaturated in the alpha-position, it being possible for this group to be substituted with one or more $C_1$-$C_{14}$ alkyl groups; it being understood that, in the case of natural ceramides or glycoceramides, $R_3$ may also be chosen from a $C_5$-$C_{26}$ alpha-hydroxyalkyl group, the hydroxyl group being optionally esterified with a $C_{16}$-$C_{30}$ alpha-hydroxy acid.

Exemplary ceramides of formula (V) which may be chosen include compounds wherein $R_1$ is chosen from a saturated or unsaturated alkyl derived from $C_6$-$C_{22}$ fatty acids; $R_2$ is chosen from a hydrogen atom; and $R_3$ is chosen from a linear, saturated $C_{15}$ group. By way of non-limiting example, such compounds may be chosen from N-linoleoyl-dihydrosphingosine, N-oleoyldihydrosphingosine, N-palmitoyldihydro-sphingosine, N-stearoyldihydrosphingosine, N-behenoyldihydrosphingosine, or mixtures thereof.

As further non-limiting examples of ceramides, compounds wherein $R_1$ is chosen from a saturated or unsaturated alkyl group derived from fatty acids; $R_2$ is chosen from a galactosyl or sulphogalactosyl group; and $R_3$ is chosen from the group —CH=CH—$(CH_2)_{12}$—$CH_3$ group, may be used. In at least one exemplary embodiment, the product consisting of a mixture of these compounds, sold under the trade name Glycocer, by the company Waitaki International Biosciences, may be used.

As further exemplary ceramides, mention may be made of the following ceramides, as described in US20110182839, incorporated by reference herein:

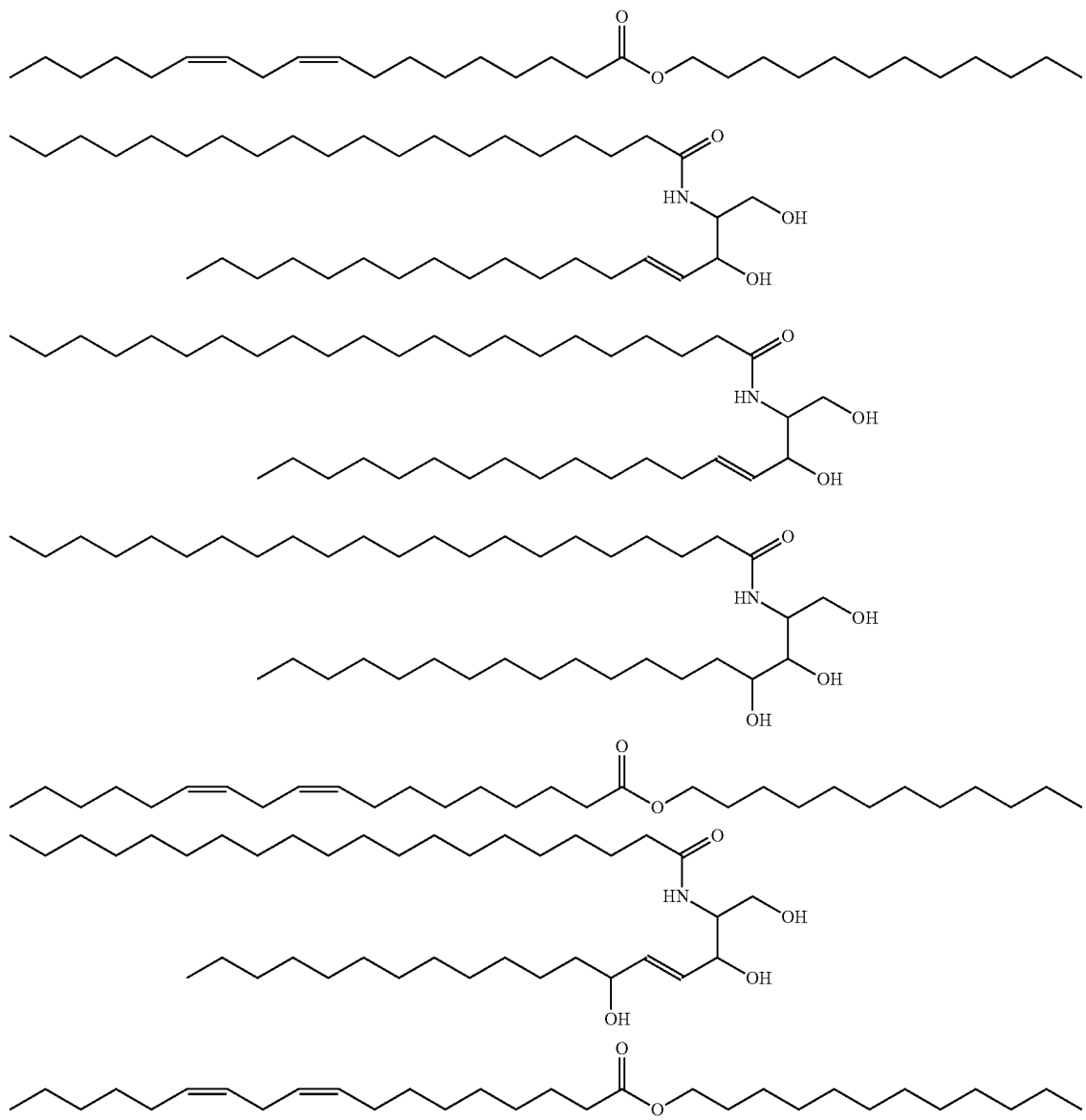

-continued

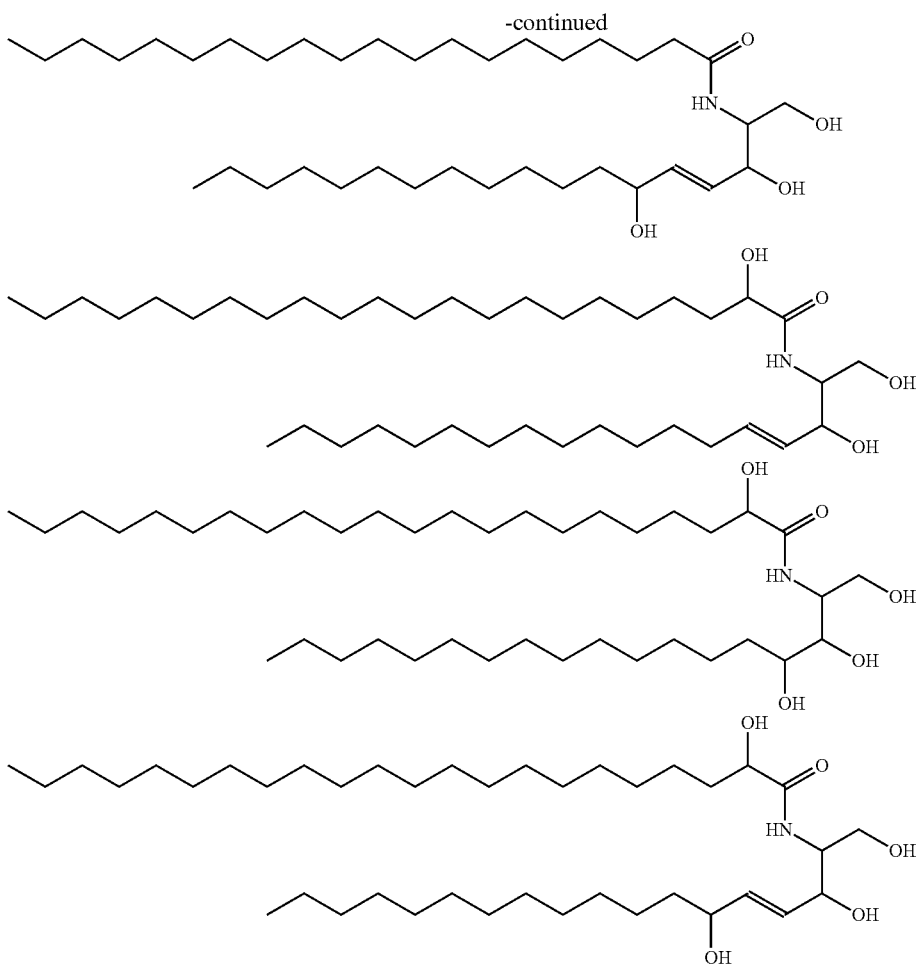

In further embodiments, ceramide compounds useful according to the disclosure may be chosen from compounds of the general formula (VI):

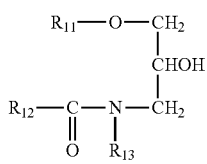

wherein, in formula (VI):
$R_{11}$ and $R_{12}$ are, independently, chosen from alkyl or alkenyl groups with 10 to 22 carbon atoms,
$R_{13}$ is an alkyl or hydroxyl alkyl group with 1 to 4 carbon atoms, and
n is a number ranging from 1 to 6, such as, for example, 2 or 3.

In at least one embodiment, the at least one ceramide compound is chosen from cetyl-PG-hydroxyethylpalmitamide. In a further embodiment, the at least one ceramide compound is chosen from propanediamide, N,N-dihexadecyl-N,N-bis-(2-hydroxyethyl), such as that sold commercially as Questamide H or Pseudoceramide H by the company Quest International Australia Pty. Ltd. In yet a further embodiment, the at least one ceramide compound is chosen from Cetyl-PG Hydroxylpalmatide/decyl glucoside/water, sold as SOFCARE P100H by Kao.

Without wishing to be bound, in at least certain exemplary embodiments, ceramides may be chosen as auxiliary ingredients for their conditioning and/or color-enhancing benefits.

In various embodiments, the at least one ceramide may be present in an amount ranging from about 0.01% to about 2% by weight, such as from about 0.01% to about 1% by weight, based on the total weight of the composition.

Alkoxyaminosilicones

Exemplary alkoxyaminosilicones that may be used according to the disclosure include, but are not limited to, alkoxyaminosilicones of the general formula (VII):

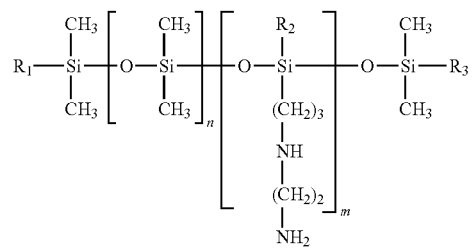

wherein, in formula (VII):
n is a number ranging from about 0 to about 999, such as, for example, from about 49 to about 249, such as from about 125 to about 175;

m is a number ranging from about 1 to about 1000, such as, for example, from about 1 to about 10, such as from about 1 to about 5; and m and n are numbers with a sum (n+m) ranging, for example, from about 1 to about 1000, such as, for example, from about 50 to about 250 and still further, for example, from about 100 to about 200; wherein $R_1$, $R_2$ and $R_3$, are independently chosen from a hydroxyl radical and $C_1$-$C_4$ alkoxy radicals, wherein at least one of the radicals $R_1$, $R_2$ and $R_3$ are chosen from alkoxy radicals.

The alkoxy radical may be, for example, a methoxy radical.

The hydroxy/alkoxy molar ratio may, for example, range from about 0.2:1 to about 0.4:1, such as, for example, from about 0.25:1 to about 0.35:1 and further, for example, may be equal to about 0.3.

The at least one aminosilicone of formula (VII) may have a weight-average molecular mass ranging, for example, from 2000 to 1,000,000, for example from 3500 to 200,000.

By way of example only, the alkoxyaminosilicone product provided by the company Wacker under the name Belsil ADM 652®, may be chosen.

Further exemplary alkoxyaminosilicones that may be used according to the disclosure include, but are not limited to, alkoxyaminosilicones of the general formula (VIII):

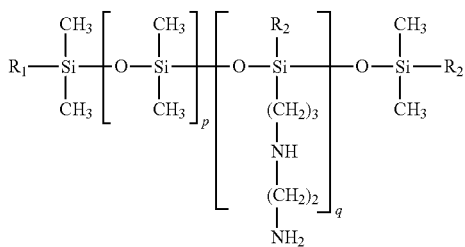

wherein, in formula (VIII):

p is a number ranging from 0 to 999, for example from 49 to 349, and further, for example, from 159 to 239;

q is a number ranging from 1 to 1000, for example, from 1 to 10, and further, for example, from 1 to 5; and p and q are numbers with a sum (p+q), for example, ranging from 1 to 1000, for example from 50 to 350 and further, for example, from 150 to 250;

$R_1$ and $R_2$ are independently chosen from a hydroxyl radical and $C_1$-$C_4$ alkoxy radicals, wherein at least one of the radicals $R_1$ and $R_2$ are chosen from alkoxy radicals.

The alkoxy radical may be, for example, a methoxy radical.

The hydroxy/alkoxy molar ratio may, for example, range from about 1:0.8 to about 1:1.1, such as, for example from about 1:0.9 to about 1:1, and may further, for example, be about 1:0.95.

The at least one aminosilicone of formula (VIII) may have a weight-average molecular mass ranging, for example, from 2000 to 200,000, for example from 5000 to 100,000, and further, for example, from 10,000 to 50,000.

The weight-average molecular mass of the at least one aminosilicone are measured by gel permeation chromatography (GPC) at ambient temperature in polystyrene equivalents. The columns used are µ Styragel columns. The eluent is THF and the flow rate is 1 ml/min. 200 µl of a 0.5% by weight solution of silicone in THF are injected. Detection may be carried out by refractometry and UV metry.

By way of example only, the alkoxyaminosilicone products provided by the company Wacker under the name Fluid WR 1300® and Belsil ADM 6057® may be chosen.

The at least one aminosilicone chosen from formulae (VII) and (VIII) may be employed, for example, in an oil-in-water emulsion. The oil-in-water emulsion may further comprise at least one surfactant. The at least one surfactant may be chosen, for example, from cationic and non-ionic surfactants.

A particle of the at least one aminosilicone in the emulsion may have an average size ranging from, for example, about 3 to about 500 nanometers. Such particle sizes are measured with a laser granulometer particle of the at least one aminosilicone in the emulsion may have an average size ranging, for example, from about 3 to about 500 nanometers. Such particle sizes are measured with a laser granulometer.

The at least one aminosilicone of formula (VIII) may be used, for example, in a microemulsion. In the microemulsion, the at least one aminosilicone of formula (VIII) may have a size ranging from 5 to 60 nanometers and, for example, from 10 to 50 nanometers.

A microemulsion of the at least one aminosilicone of formula (VIII) may be available, for example, under the name Finish CT 96 E® or SLM 28020® by the company Wacker.

The at least one aminosilicone chosen from formulae (VII) and (VIII) may be selected, for example, such that the contact angle with water of a hair treated with a composition comprising 2% AS (active substance) of the at least one aminosilicone ranges from 90° C. to 180° C., for example from 90° C. to 130° C.

A composition comprising the at least one aminosilicone chosen from formulae (VII) and (VIII) may be such that the contact angle of a hair treated with the composition ranges from 90° C. to 180° C., for example from 90° C. to 130° C.

The measurement of the contact angle described herein may be performed as described in U.S. Pat. No. 6,846,333, incorporated by reference herein. For example, the product SLM 28020® from Wacker at 12% in water (i.e. 2% of at least one aminosilicone) gives a contact angle of 93° C.

In at least certain exemplary embodiments, the alkoxyaminosilicone may be provided as part of the composition Wacker-Belsil ADM Log 1® (Wacker Chemie AG (Munich, Germany)), which consists of amodimethicone at 15%, Glycerin at 3.5%, Trideceth-5 at 6% and Trideceth-10 at 1.5%, or as part of the cationic aqueous emulsion Dow Corning 2-8299 Cationic Emulsion (Dow Corning).

Without wishing to be bound, in at least certain exemplary embodiments, alkoxyaminosilicones may be chosen as auxiliary ingredients for their conditioning, fade-resistance, and/or porosity-reducing benefits, and/or for their ability to impart improved cosmetic properties to the hair, such as, for example, softness, smoothness, and/or ease of disentangling and styling.

In various embodiments, the at least one alkoxyaminosilicone may be present in an amount ranging from about 0.01% to about 20% by weight, such as from about 0.1% to about 15% by weight, from about 0.5% to about 10% by weight, based on the total weight of the composition.

Silane Compounds

Exemplary silanes that may be used according to various embodiments of the disclosure include, but are not limited to, organosilanes and derivatives thereof, such as alkylsilanes, allylsilanes, alkoxysilanes, and the like.

In various exemplary embodiments, the at least one silane compound may be chosen from alkoxysilanes comprising at least one solubilizing functional group. By way of non-limiting examples, silanes may be chosen from methoxysilanes, triethoxysilanes, and the like such as aminopropyltriethoxysilane, methyltriethoxysilane, and derivatives thereof.

As used herein, the term "at least one solubilizing functional group" means any functional chemical group facilitating the bringing into solution of the alkoxysilane in the solvent or in a combination of solvents of the composition, for example, in solvents chosen from water, water-alcoholic mixtures, organic solvents, polar solvents and non-polar solvents.

Suitable solubilizing functional groups include, but are not limited to, primary, secondary, and tertiary amine, aromatic amine, alcohol, carboxylic acid, sulfonic acid, anhydride, carbamate, urea, guanidine, aldehyde, ester, amide, epoxy, pyrrole, dihydroimidazole, gluconamide, pyridyle, and polyether groups.

The at least one alkoxysilane comprising at least one solubilizing functional group present in the composition may, in at least one embodiment, comprise two or three alkoxy functions. In another embodiment, the alkoxy functional groups are chosen from methoxy and ethoxy functional groups.

According to a further embodiment, the at least one alkoxysilane comprising at least one solubilizing functional group present in the composition of the present disclosure is chosen from compounds of formula (IX):

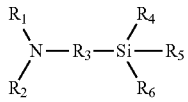

wherein, in formula (IX):
$R_4$ is chosen from halogen atoms, OR' groups, and $R_{11}$ groups;
$R_5$ is chosen from halogen atoms, OR'' groups, and $R_{12}$ groups;
$R_6$ is chosen from halogen atoms, OR''' groups, and $R_{13}$ groups;
$R_1$, $R_2$, $R_3$, R', R'', R''', $R_{11}$, $R_{12}$, and $R_{13}$, which may be identical or different, are chosen from linear and branched, saturated and unsaturated hydrocarbon groups, optionally bearing at least one additional chemical group, wherein $R_1$, $R_2$, R', R'', and R''' may also be chosen from hydrogen; at least two groups $R_4$, $R_5$, and $R_6$ are different from $R_{11}$, $R_{12}$, and $R_{13}$, and at least two groups R', R'', and R''' are not hydrogen.

The at least one alkoxysilane comprising at least one solubilizing functional group may also be chosen from compounds of formula (X):

wherein, in formula (X):
$R_9$ is chosen from halogen atoms and OR'$_9$ groups and $R_{10}$ is chosen from halogen atoms and OR'$_{10}$ groups; wherein at least one of $R_9$ and $R_{10}$ is not a halogen;
R'$_9$ and R'$_{10}$, which may be identical or different, are chosen from hydrogen, and linear and branched, saturated and unsaturated $C_1$-$C_{14}$ hydrocarbon groups; wherein at least one of $R_9$ and $R_{10}$ is not hydrogen;
$R_7$ is a non hydrolyzable functional group providing a cosmetic effect, and
$R_8$ is a non hydrolyzable functional group bearing at least one function chosen from: amines, carboxylic acids and salts thereof, sulfonic acids and salts thereof, polyols such as glycol, polyethers such as polyalkylene ether, and phosphoric acids and salts thereof.

As used herein, the term "functional group providing a cosmetic effect" means a group derived from an entity chosen from reducing agents, oxidizing agents, coloring agents, polymers, surfactants, antibacterial agents, and UV absorbing filters.

According to a third embodiment, the at least one alkoxysilane comprising at least one solubilizing functional group may be chosen from compounds of formula (XI):

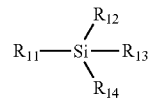

wherein, in formula (XI):
$R_{12}$ is chosen from halogen atoms, OR'$_{12}$ groups, and $R_O$ groups;
$R_{13}$ is chosen from halogen atoms, OR'$_{13}$ groups, and R'$_O$ groups;
$R_{14}$ is chosen from halogen atoms, OR'$_{14}$ groups, and R''$_O$ groups;
wherein at least two groups $R_{12}$, $R_{13}$ and $R_{14}$ are different from $R_O$, R'$_O$, and R''$_O$ groups;
$R_{11}$ is a group chosen from groups bearing at least one function chosen from: carboxylic acids and salts thereof, sulfonic acids and salts thereof, and polyalkylethers; and
Ro, R'o, R''o, R'$_{12}$, R'$_{13}$, and R'$_{14}$, which may be identical or different, are chosen from linear and branched, saturated and unsaturated, $C_1$-$C_{14}$ hydrocarbon groups optionally bearing at least one additional chemical functional group chosen from: carboxylic acids and salts thereof, sulfonic acids and salts thereof, and polyalkylether functions, wherein R'$_{12}$, R'$_{13}$, and $R_{14}$ may also be chosen from hydrogen, and wherein at least two of the groups R'$_{12}$, R'$_{13}$, and R'$_{14}$ are not hydrogen.

According to another embodiment, the at least one alkoxysilane comprising at least one solubilizing functional group may be chosen from compounds of formula (XII):

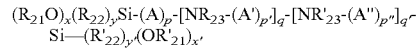

wherein, in formula (XII):
$R_{21}$, $R_{22}$, R'$_{21}$, and R'$_{22}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups,
x is an integer ranging from 1 to 3,
y=3-x,
x' is an integer ranging from 1 to 3,
y'=3-x',
p, p', p'', q, and q' can each be 0 or 1, wherein at least one of q or q' is not equal to zero, A, A', and A", which may be identical or different, are chosen from linear and branched $C_1$-$C_{20}$ alkylene divalent radicals, and $R_{23}$ and $R'_{23}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from $C_3$-$C_{20}$ alcohol ester, amine, amide, carboxyl, alkoxysilane, hydroxyl, carbonyl, and acyl groups.

The at least one alkoxysilane comprising at least one solubilizing functional group may also be chosen from compounds of formula (XIII):

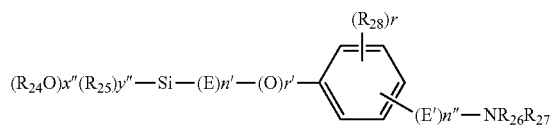

wherein, in formula (XIII):
$R_{24}$ and $R_{25}$, which may be identical or different, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, x"=2 or 3,
y"=3-x",
n'=0 or 1,
n"=0 or 1, E and E', which may be identical or different, are chosen from linear and branched $C_1$-$C_{20}$ alkylene divalent radicals, $R_{26}$ and $R_{27}$, which may be identical or different, are chosen from hydrogen and linear and branched, saturated and unsaturated hydrocarbon chains, optionally comprising at least one heteroatom, optionally interrupted by or substituted with at least one entity chosen from: ether, $C_1$-$C_{20}$ alcohol ester, amine, carboxyl, alkoxysilane, $C_6$-$C_{30}$ aryl, hydroxyl, and carbonyl groups, and aromatic, heterocyclic, and non-heterocyclic rings, optionally substituted with at least one group chosen from: $C_1$-$C_{20}$ alcohol ester, amine, amide, carboxyl, alkoxysilane, hydroxyl, carbonyl, and acyl groups, r is an integer ranging from 0 to 4,
r'=0 or 1, and $R_{28}$, which may be identical or different, is chosen from hydrogen and linear and branched, saturated and unsaturated hydrocarbon chains, comprising, optionally at least one heteroatom, optionally interrupted by or substituted with at least one entity chosen from: ether, alkyl alcohol ester, amine, carboxyl, alkoxysilane, alkyl aryl, hydroxyl, and carbonyl groups, and aromatic, heterocyclic, and non-heterocyclic rings.

According to a further exemplary embodiment, the at least one alkoxysilane comprising at least one solubilizing functional group may be chosen from compounds of formula (XIV):

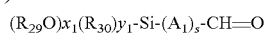

wherein, in formula (XIV):
$R_{29}$ and $R_{30}$, independently, are chosen from linear and branched, saturated and unsaturated hydrocarbon chains, optionally comprising at least one heteroatom, optionally interrupted by or substituted with at least one group chosen from ether, ester, amine, amide, carboxyl, hydroxyl, and carbonyl groups, $x_1$=2 or 3,
$y_1$=3-$x_1$, $A_1$ is chosen from linear and branched $C_1$-$C_{20}$ alkylene divalent radicals, optionally interrupted by or substituted with at least one group chosen from $C_1$-$C_{30}$ alcohol ester, amine, carboxyl, alkoxysilane, $C_6$-$C_{30}$ aryl, hydroxyl, and carbonyl groups, and s=0 or 1.

In a further exemplary embodiment, the at least one alkoxysilane comprising at least one solubilizing functional group is chosen from compounds of formula (XV):

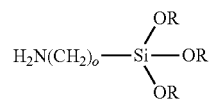

wherein, in formula (XV), the R radicals, which may be identical or different, are chosen from $C_1$-$C_6$ alkyl radicals and n is an integer ranging from 1 to 6, for example, from 2 to 4.

The alkoxysilanes useful in the present disclosure can be chosen from alkoxysilanes comprising a silicon atom of formula $R_{(4-n)}SiX_n$, wherein X is a hydrolysable group such as methoxy, ethoxy or 2-methoxyethoxy, R is a monovalent organic radical which contains 1 to 12 carbon atoms and may contain groups such as mercapto, epoxy, acrylyl, methacrylyl, amino or urea, and n is an integer from 1 to 4, and according to at least one embodiment is 3. Exemplary alkoxysilanes include, but are not limited to, 3-mercaptopropyltriethoxysilane and aminoalkyltrialkoxysilanes such as 3-aminopropyltriethoxysilane, as described in French Patent Application No. FR2789896, incorporated by reference herein.

Other useful alkoxysilanes are cited, for example, in EP1216022, incorporated by reference herein, which describes alkoxysilanes comprising at least one hydrocarbon chain containing a non-basic solubilizing chemical function. In this respect, non-limiting mention may be made of the HCl-neutralized sodium N-[(3-trimethoxysilyl)propyl]ethylenediaminetriacetate supplied by GELEST.

According to at least one embodiment, the alkoxysilanes may comprise at least one hydrocarbon chain containing fluorine atoms. Possible examples include but are not limited to the 3,3,3-trifluoropropyltriethoxysilane or tridecafluorooctyltriethoxysilane compounds described in EP1510197, incorporated by reference herein.

In another embodiment, the useful alkoxysilanes may be alkoxysilanes which carry a group having a cosmetic functional group, such as aromatic nitro dyes or anthraquinone, napthoquinone, benzoquinone, azo, xanthene, triarylmethane, azine, indoaniline, indophenolic or indoamine dyes; groups having a reductive effect, such as thiol groups, sulphinic acid or sulphinic salt, it being possible for these alkoxysilanes to carry a solubilizing non-hydrolysable group such as amino groups, carboxylic acids, sulphonic acids, sulphates, quaternary ammoniums, polyalcohols, polyether and phosphates. One possible example includes aminopropyl-N-(4,2-dinitrophenyl)aminopropyldiethoxysilane. Exemplary compounds of this type are described, for example, in EP1216023, incorporated by reference herein.

The alkoxysilanes of the present disclosure may be amino aryl alkoxysilanes. Non-limiting examples include the following, all of which are provided by GELEST:

3-(m-aminophenoxy)propyltrimethoxysilane, of the formula:

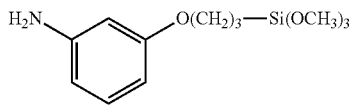

p-aminophenyltrimethoxysilane, of formula:

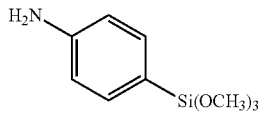

and

N-(2-aminoethylaminomethyl)phenethyltrimethoxysilane, of the formula:

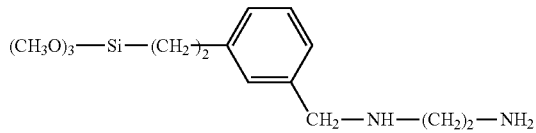

The alkoxysilanes of the present disclosure may be silanes having an aldehyde or acetal functional group.

The alkoxysilanes may also be silanes containing non-primary amines, such as the bis[3-(triethoxysilyl)propyl] amine of the formula $(CH_3CH_2O)_3$—$Si(CH_2)_3NH(CH_2)_3Si(OCH_2CH_3)_3$ provided by Fluorochem, the bis[trimethoxysilylpropyl]amine of the formula $(CH_3O)_3$—$Si(CH_2)_3NH(CH_2)_3Si(OCH_3)_3$ provided by Gelest, the bis[methyldiethoxysilylpropyl]amine of the formula $(CH_3CH_2O)_2CH_3Si(CH_2)_3NH(CH_2)_3SiCH_3(OCH_2CH_3)_2$ provided by Gelest and the bis[3-trimethoxysilylpropyl] ethylenediamine of formula $(CH_3O)_3Si(CH_2)_3NH(CH)_2NH(CH_2)_3Si(OCH_3)_3$ provided by Gelest.

In other exemplary embodiments, the silane compound may be chosen from octadecyltrichlorosilane and derivatives thereof.

In other various exemplary embodiments, the at least one silane compound may be chosen from those described in US 20080184495, incorporated by reference herein, including, for example, alkoxysilane compounds comprising at least one —Si—OR portion, wherein R is an alkyl group comprising from 1 to 6 carbon atoms.

By way of example, the at least one silane may be chosen from organosiloxanes comprising at least 2 alkoxysilane end groups and/or trialkoxysilane end groups.

In at least one exemplary embodiment, the at least one silane may be chosen from Bis-PEG-18 Methyl Ether Dimethyl Silane, sold by Dow Corning.

In another exemplary embodiment, the at least one silane is a trialkoxysilane comprising an amino substituent.

In particularly preferred exemplary embodiments, the at least one silane is γ-aminopropyltriethoxysilane, also known as 3-aminopropyltriethoxysilane, commercially available under the tradename, KBE-903™, from Shin-Etsu, and also under the tradename, Silsoft® A-1100, from Momentive Performance Materials.

In various embodiments, the at least one silane may be present in an amount ranging from about 0.1% to about 40% by weight, such as from about 0.1% to about 30% by weight, from about 0.5% to about 30% by weight, from about 0.5% to about 25% by weight, or from about 1% to about 20% by weight, based on the total weight of the composition.

Activators

According to various embodiments of the disclosure, one or more phases of the compositions described herein may comprise at least one activator. Without wishing to be bound by theory, it is believed that activators increase the lightening effect of other components, thereby providing compositions having superior lightening power in less time, and therefore minimizing the damage to the hair and/or skin. This is likewise believed to be even more useful when, as in various embodiments herein, successive chemical treatments are applied to the hair in a short period of time.

Exemplary activators that may be used according to various embodiments of the disclosure include, but are not limited to, cationic pyridinium derivatives, such as those disclosed in WO2010054981; cationic acylpyridinium derivatives, such as those disclosed in US2011232669, US2011047712, and US2011146006; saccharin derivatives, such as those disclosed in DE102010043497; cationic phthalamide derivatives, such as those disclosed in WO2011079974; cationic 3,4-dihydroisoquinolinium derivatives, such as those disclosed in US2011146005; sulfonimine derivatives, such as those disclosed in WO2011064007; 1,2-dihydropyrimidinium derivatives, such as those disclosed in DE102006031470; diacylated 2,5-diketopiperizine derivatives, such as those disclosed in U.S. Pat. No. 3,775,332; N-acylated-2,4,6,8-tetraazabicyclo-(3,3,1)-nonan-3,7-diones, such as those disclosed in U.S. Pat. No. 3,825,543; and acylated glycoluril derivatives, such as those disclosed in U.S. Pat. No. 3,715,184, all of which are incorporated by reference herein.

Other exemplary activators that may be used in the composition include, but are not limited to, aliphatic and carboxylic activators. In various embodiments, activators contain a hydroxyl group, a carboxylic acid, a sulfuric acid monoester, a phosphoric acid monoester, and/or a physiologically acceptable salt thereof.

By way of example, activators may be chosen from compounds of the general formula (XVI):

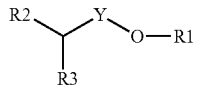

wherein, in formula (XVI):
Y is a carbonyl group, a direct bond or methylene group;
R1 is hydrogen, a $C_1$-$C_4$ alkyl group, a physiologically acceptable cation or an $SO_3^-$ or a $PO_3^{2-}$ group;
R2 is an amino, a methylamino, a dimethylamino, a trimethylammonio group, phenyl, benzyl, phenoxymethyl, 1-naphthyl, 2-naphthyl, 2-, 3-, 4-toluoyl, or an R4-O—$(CH_2CH_2O)_n$ group, wherein R4 is a $C_6$-$C_{20}$ alkyl group and n is a number 15 or greater; and R3 is hydrogen or an optionally branched $C_1$-$C_6$ alkyl group;
provided that:
if Y is a carbonyl group, R1 is hydrogen, a $C_1$-$C_4$ alkyl group or a physiologically acceptable cation, R2 is an amino, a methylamino, a dimethylamino or a trimethylammonio group, and R3 is hydrogen or an optionally branched $C_1$-$C_6$ alkyl group;
if Y is a direct bond, R1 is hydrogen, R2 is phenyl, benzyl, phenoxymethyl, 1-naphthyl, 2-naphthyl, 2-, 3- or 4-toluoyl, and R3 is hydrogen or an optionally branched $C_1$-$C_6$ alkyl group; or
if Y is a methylene group, R1 is an $SO_3^-$ or a $PO_3^{2-}$ group, R2 is an R4-O—$(CH_2CH_2O)_n$ group, wherein R4 is a $C_6$-$C_{20}$ alkyl group and n is a number greater than 15, and R3 is hydrogen.

Non-limiting examples of activators useful according to embodiments of the disclosure include activators such as glycine, N-methyl glycine, N,N-dimethyl glycine, alanine, N-methyl alanine, N,N-dimethyl alanine, leucine, N-methyl leucine, N,N-dimethyl leucine, isoleucine, N-methyl isoleucine, N,N-dimethyl isoleucine, and physiologically acceptable salts thereof.

In various embodiments, the activator may be chosen from glycine, aromatic alcohols, and physiologically acceptable salts thereof. Exemplary and non-limiting aromatic alcohols may include benzyl alcohol, 2-phenylethyl alcohol, 1-phenylethyl alcohol, 2-phenoxyethanol, 1-hydroxymethylnaphthalene and/or 2-hydroxymethylnaphthalene.

In further exemplary embodiments, activators may be chosen from physiologically acceptable salts of an alkyl ether sulfate having the general formula (XVII):

wherein, in formula (XVII), R4 is a $C_6$-$C_{20}$ alkyl group; m is a number from 15 or greater; and Y is an alkali metal and/or alkaline earth metal, ammonium, alkylammonium or alkanolammonium.

In at least one exemplary embodiment, the activator may be Sodium Coceth-30 Sulfate and is distributed by Cognis as a 31-33 wt % aqueous solution under the trade name Disponil® FES 77.

In embodiments where the activator contains a structural unit which allows a plurality of spatial arrangements, such as substituted double bonds or centers of asymmetry, it is understood that all possible stereoisomers are included. It may optionally, however, also be possible to use either just one stereoisomer, or a mixture of two or more stereoisomers.

In various embodiments, the at least one activator may be present in an amount ranging from about 0.01% to about 15% by weight, such as from about 0.1% to about 12% by weight, from about 0.5% to about 10% by weight, or from about 1% to about 5% by weight, based on the total weight of the composition.

Lift-Enhancing Agents

In addition to the lift-enhancing agents described above, exemplary lift-enhancing agents that may be used as auxiliary ingredients include, but are not limited to, metal catalysts, such as, for example, magnesium hydroxide and magnesium carbonate.

Other Ingredients

The compositions of the present invention can also comprise any additive typically used in cosmetic or hair treatment compositions. Such additives can be present in the pre-alkalizing composition, the color-altering composition, and/or the post-treatment composition. Exemplary additives may include waxes, organogelators, thickening agents such as organophilic clays, dispersants, oils, preserving agents, fragrances, fillers, neutralizing agents, hydroxy acids, UV filters, acidifying agents, buffering agents, conditioning agents, surfactants, antioxidants, fragrances, vitamins, and provitamins.

The composition according to the invention may comprise one or more natural dyes. Non-limiting examples of natural dyes that may be chosen include lawsone, juglone, alizarin, purpurin, carminic acid, kermesic acid, laccaic acid, purpurogallin, anthragallol, protocatechaldehyde, indigo, isatin, curcumin, spinulosin, chlorophylls, chlorophyllines, orceins, haematin, haematoxylin, brazilin, brazileine, safflower dyes (for instance carthamine), flavonoids (with, for example, morin, apigenidin and sandalwood), anthocyans (of the apigeninidin type), carotenoids, tannins, sorghum and cochineal carmine, or mixtures thereof.

Extracts or decoctions containing these natural dyes, and especially henna-based extracts, may also be used.

For example, the natural dyes are chosen from lawsone, juglone, alizarin, purpurin, carminic acid, kermesic acid, laccaic acid, purpurogallin, protocatechaldehyde, indigo, isatin, curcumin, spinulosin, apigenidin, chlorophylline, sorghum, orceins, cochineal carmine, haematin, haematoxylin, brazilin and brazileine, and mixtures thereof.

These dyes may optionally be used in the presence of mordants (for example zinc, manganese, aluminium, iron, etc. salts).

The natural dyes, when they are present, may, for example, represent from about 0.001% to about 10% by weight, such as from about 0.01% to about 8% by weight, or from about 0.1% to about 5% by weight, relative to the weight of the composition.

Needless to say, a person skilled in the art will take care to select the optional additional compound(s) mentioned above such that the advantageous properties intrinsically associated with the methods and compositions of the present invention disclosed herein are not, or are not substantially, adversely affected by the envisaged addition(s).

Heat Treatment

As an additional, optional step, for example during or after one or more of steps (a), (c), or (d), above, such as subsequent to the application of the color-altering composition, the hair may be treated with heat. The heat treatment may optionally be effectuated by any means known, such as, for example, by use of a hair dryer/hood, hot/flat iron, exposure to ultraviolet (UV) light, etc.

The step of exposing the hair to heat may last for any amount of time, such as about 0.1 second to about 1 hour, for example from about 5 minutes to about 50 minutes, about 10 to about 45 minutes, such as about 30 minutes. In various embodiments, the heat treatment may be at a temperature of at least about 50° C., such as at least about 75° C., at least about 100° C., or at least 150° C. By way of example, the temperature may range from about 50° C. to about 250° C.

The heat treatment may optionally be accompanied by a smoothing step.

Application

The compositions according to various embodiments of the disclosure may be in any form known to those of skill in the art, and may be applied to the hair by any method known. By way of example only, the compositions may be provided in a multiple-agent container, e.g. as a foam.

In at least one exemplary embodiment, methods for altering the color of hair comprise discharging a composition as described herein in the form of a foam from a squeeze container, aerosol container, and the like, for example as described in WO2008136433, GB2219352A, JP5155742A2, and US20030084517, all of which are incorporated by reference herein.

According to various embodiments disclosed herein, the color-altering composition is applied to the pre-alkalized hair without the use of a developer. Conventional dyeing processes often require the pre-mixing of the color-altering composition with a developer, such as hydrogen peroxide, followed by the application of the mixture to the hair fibers. These processes may be messy and/or time-consuming. In contrast, the methods disclosed herein may allow the hair color to be developed in situ, e.g., directly on the hair fibers without the need for a developer.

Unless expressly indicated otherwise, all numeric quantities are to be understood as being modified in all instances by the term "about," whether or not so stated, meaning within 10% of the indicated number.

As used herein, the expressions "substantially free" and "substantially no" are to be understood as meaning less than about 0.05 wt % of the indicated compound, relative to the total weight of the composition. For instance, a color-altering composition comprising substantially no chemical oxidizing agents is understood to mean a composition comprising less than about 0.05 wt % of chemical oxidizing agents, relative to the total weight of the color-altering composition. By way of non-limiting example, the color-altering composition may comprise less than about 0.04 wt %, such as less than about 0.03 wt %, less than about 0.02 wt %, or less than about 0.01 wt % of chemical oxidizing agents, relative to the total weight of the composition.

As used herein, the expression "at least one" means one or more and thus includes individual components as well as mixtures/combinations. As used herein, the terms "a," "an," and "the" are meant to signify "at least one," unless expressly otherwise indicated. Thus, the phrase "a direct dye" means one or more direct dyes.

As used herein, the term "hair" is meant to include keratinous fibers. As used, the term "hair" may include "living" hair, i.e. on a living body, or may be "non-living" i.e. in a wig, hairpiece or other aggregation of non-living fibers, such as though used in textiles and fabrics. Mammalian hair, e.g. human hair, is preferred in various embodiments. However wool, fur and other melanin-containing fibers are suitable for use in the methods and with the compositions described herein.

The term "anhydrous" as used herein is intended to mean that the composition is either completely free of unbound water or contains substantially no unbound water, such as, for example, no more than about 1% by weight, such as no more than about 0.5% by weight, based on the weight of each composition.

As used herein, the phrase "salts and derivatives thereof" is intended to mean all salts and derivatives comprising the same functional structure as the compound they are referring to, and that have similar properties.

As used herein, the terms "pre-alkalizing" and "pre-alkalized" mean that the hair has a higher pH than when it has not been subjected to chemical treatment, as described herein. In certain embodiments, the pH of the pre-alkalized hair may be greater than about 7, for example, ranging from about 7 to about 14, from about 7.5 to about 14, or from about 8 to about 14.

As used herein, the phrase "color-altering composition" means a composition that brings about a change in hair color, including, for example, bleaching, lightening, dyeing, etc.

As used herein, the phrase "minimizing damage" to the hair and/or skin is intended to mean that the breakage of the hair has been reduced or eliminated.

As used herein, the term "ready-to-use composition" means a composition intended to be applied in unmodified form to the keratin fibers, i.e. it may be stored in unmodified form before use or may result from the extemporaneous mixing of two or more compositions.

As used herein, the expression "chemically altering" means contacting the hair with at least one composition containing at least one chemical ingredient that changes or contributes to changing the shape and/or the color of the hair, to any degree.

As used herein, the term "applying" a composition to the hair or "treating" the hair with a composition is intended to mean contacting the hair with at least one of the compositions of the invention, in any manner.

As used herein, the terms "straightening" or "straighten" or "relaxing" or "relax" the hair mean to remove the curl from the hair or reduce the degree of curl of the hair. It also means changing the shape of hair or the degree of curl in the hair to make the hair more straight. It can also mean removing or reducing the frizziness of the hair.

As used herein, "cosmetically acceptable" means that the item in question is compatible with any human keratin material and in particular human keratinous fibers, such as human hair.

As used herein, "cosmetically acceptable carrier" means a carrier that is compatible with any human keratin material and in particular human keratinous fibers, such as human hair.

As used herein, "recently contacted" means that the time period between contacting the hair with a chemical composition according to various methods is not more than about twenty four hours.

As used herein, "natural hair color" refers to the color of hair resulting from the melanin pigments present in the hair.

As used herein, "conditioning" means imparting to at least one keratinous fiber at least one property chosen from combability, manageability, moisture-retentivity, luster, shine, and softness. In case of combing, the level of conditioning is evaluated by measuring, and comparing, the ease of combability of the treated hair and of the untreated hair in terms of combing work (gm-in).

As used herein, "formed from," means obtained from chemical reaction of, wherein "chemical reaction," includes spontaneous chemical reactions and induced chemical reactions. As used herein, the phrase "formed from", is open ended and does not limit the components of the composition to those listed.

As used herein, the term "rheology-modifying agent" or "rheology modifier" means any compound capable of giving a viscosity to a composition such that, once it is applied onto hair, this composition does not run, and remains perfectly localized at the point of application.

As used herein, the methods and compositions disclosed may be used on the hair that has not been artificially dyed or pigmented.

As used herein, the methods and compositions disclosed may be also used on the hair that has been artificially dyed or pigmented.

It is to be understood that the foregoing describes various exemplary embodiments of the invention, but that modifications may be made therein without departing from the spirit or scope of the invention as set forth in the claims.

EXAMPLE

| Color Altering Composition | | | |
|---|---|---|---|
| INCI Name | Commercial Name | % activity | Concentration wt (%) |
| Laureth-12 | Alkonat L 120 (Oxiteno) | 100 | 3 |
| Oleth-30 | Genapul U 300 F (Clariant) | 100 | 2 |
| Sodium Cetearyl Sulfate | Lanette e Granules (Cognis) | 96 | 1.5 |
| Cetearyl Alcohol | N/A | | 2 |
| Sodium Sulfate | N/A | | 2 |
| Laureth-2 | Arylpon F (Cognis) | 100 | 8 |
| PEG-4 Rapeseedamide | Amidet N (Kao) | 92.305 | 4 |
| Trideceth-2 | Amidet A15/Lao 15 (Kao) | 100 | 4 |
| Glycerin | Glycerine 4833 (Oleon) | 100 | 3 |
| Polyquaternium-6 | Merquat 100 polymer (Nalco) | 40 | 2 |
| 3-Nitro-p-Hydroxyethylaminophenol | NHEAP PREMIUM GRADE (Artec) | 100 | 0.3 |
| 4-Amino-3-Nitrophenol | 4-AMINO-3-NITRO PHENOL (IMEXINE FN) (Dragon Chemical) | 100 | 0.4 |
| HC Yellow No. 9 | IMEXINE FAD (Chimex) | 100 | 0.2 |
| HC Red No. 3 | HC Red 3 (Lowenstein) | 100 | 0.6 |
| Cetyl Hydroxyethylcellulose | Natrolsol Plus 330 C S (Ashland) | 100 | 0.4 |
| MEA | Monoethanolamine (Oxiteno) | | pH adjuster |
| Deionized water | N/A | 100 | QS |

Comparative Procedures A1 and A2

Virgin hair samples comprising 90% gray fibers were dyed with the color-altering composition, in the absence of a developer. The color-altering composition was left in contact with the hair fibers for 20 minutes and then washed from the hair using a standard neutralizing shampoo. In procedure A1, the color-altering composition did not comprise glycine. In procedure A2, the color-altering composition comprised 5 wt % glycine (Ajinomoto).

Comparative Procedures B1 and B2

Virgin hair samples comprising 90% gray fibers were dyed with a 1:1 mixture of the color-altering composition and a peroxide developer comprising 6 wt % of a 50/50 hydrogen peroxide solution. The mixture was left in contact with the hair fibers for 20 minutes and then washed from the hair using a standard neutralizing shampoo. In procedure B1, the color-altering composition did not comprise glycine. In procedure B2, the color-altering composition comprised 5 wt % glycine (Ajinomoto).

Inventive Procedures C1 and C2

Relaxed (pre-alkalized, pH=7.7) hair samples comprising 90% gray fibers were dyed with the color-altering composition, in the absence of a developer. The color-altering composition was left in contact with the hair fibers for 20 minutes and then washed from the hair using a standard neutralizing shampoo. In procedure C1, the color-altering composition did not comprise glycine. In procedure C2, the color-altering composition comprised 5 wt % glycine (Ajinomoto).

Comparative Procedures D1 and D2

Relaxed (pre-alkalized, pH=7.7) hair samples comprising 90% gray fibers were dyed with a 1:1 mixture of the color-altering composition and peroxide developer. The mixture was left in contact with the hair fibers for 20 minutes and then washed from the hair using a standard neutralizing shampoo. In procedure D1, the color-altering composition did not comprise glycine. In procedure D2, the color-altering composition comprised 5 wt % glycine (Ajinomoto).

Evaluation

A colorimetric evaluation of the hair fibers was performed with a DataColor SF600X spectrocolorimeter using the CIELab system. According to this system, L indicates the lightness of the hair, where a more intense hair color is indicated by a lower L value. dE indicates the degree of lightening of the hair, representing the difference in color between the treated and untreated fibers. A more intense hair lightening is indicated by a higher dE value. dE is calculated as follows:

$$dE = \sqrt{(L-L_o)^2 + (a-a_o)^2 + (b-b_o)^2}$$

where L, a, and b represent the values measured for untreated fibers and $L_o$, $a_o$, and $b_o$ represent the values measured for treated fibers. The following results were obtained.

| Virgin Hair Samples | | | | | |
|---|---|---|---|---|---|
| | L | A | b | dE | Hair pH |
| Control - 90% gray Virgin | 60.09 | 0.53 | 13.61 | — | 5.3 |
| A1 (no developer, no glycine) | 32.26 | 26.11 | 18.41 | 38.1 | 6.1 |
| A2 (no developer, glycine) | 37.25 | 25.45 | 21.39 | 34.69 | 6.5 |

-continued

Virgin Hair Samples

| | L | A | b | dE | Hair pH |
|---|---|---|---|---|---|
| B1 (1:1 peroxide developer, no glycine) | 35.55 | 26.25 | 20.47 | 36.2 | 6.1 |
| B2 (1:1 peroxide developer, glycine) | 34.21 | 23.49 | 19.36 | 35.07 | 6 |

Relaxed Hair Samples

| | L | A | b | dE | Hair pH |
|---|---|---|---|---|---|
| Control - 90% gray Relaxed | 56.23 | 0.63 | 22.85 | — | 7.7 |
| C1 (no developer, no glycine) | 22.18 | 19.92 | 9.18 | 41.45 | 7.3 |
| C2 (no developer, glycine) | 24.7 | 22.12 | 11.46 | 39.82 | 6.6 |
| D1 (1:1 peroxide developer, no glycine) | 27.07 | 24.6 | 14.88 | 38.58 | 5.9 |
| D2 (1:1 peroxide developer, glycine) | 26.59 | 25.83 | 14.96 | 39.7 | 6.2 |

Discussion

It was noted that the relaxed hair samples exhibited an alkaline pH (7.7) before dyeing, whereas the virgin hair samples exhibited an acidic pH (5.3) before dyeing. Furthermore, it was noted that the relaxed hair samples were generally more intensely dyed (lower L value) and more effectively lightened (higher dE value), as compared to the virgin hair samples. Without wishing to be bound by theory, it is believed that the pre-alkalizing step opens the hair cuticle, thereby rendering it more susceptible to penetration by the color-altering composition.

Traditional hair dyeing methods employing peroxide developers (D1 and D2) generally dye and/or lighten the hair effectively, but can be messy, time-consuming, and/or damaging to the hair. It would therefore be desirable to develop dyeing methods not employing such developers. According to the inventive methods disclosed herein (C1 and C2), the use of peroxide developers and the drawbacks associated therewith can be avoided while also providing improved color intensity and lightening. Hair fibers dyed according to the inventive methods (C1 and C2) are more intensely dyed (lower L value) and more effectively lightened (higher dE value) as compared to fibers dyed according to methods employing peroxide developers (D1 and D2).

It is to be understood that the foregoing describes various exemplary embodiments of the invention, but that modifications may be made therein without departing from the spirit or scope of the invention as set forth in the claims.

The invention claimed is:

1. A method of altering the appearance of hair, said method comprising:
   (a) applying, onto the hair, a pre-alkalizing composition having a pH of from about 8 to about 14, wherein the pre-alkalizing composition changes the shape of the hair, and wherein the pre-alkalizing composition is left on the hair for a time period sufficient to form pre-alkalized hair having an alkaline pH;
   (b) optionally, rinsing the hair;
   (c) shampooing the hair and rinsing the shampooed hair;
   (d) applying a color-altering composition onto the pre-alkalized hair, wherein the color-altering composition comprises, in a cosmetically acceptable carrier:
      (i) at least one direct dye; and
      (ii) optionally at least one oxidative dye precursor;
   and wherein the pH of the color-altering composition ranges from about 1 to about 7;
   (e) leaving the color-altering composition on the hair for a time period sufficient to achieve a desired level of color lift; and
   (f) optionally, rinsing the hair;
   wherein the color-altering composition does not comprise a chemical oxidizing agent; and
   wherein the color-altering composition is applied onto the pre-alkalized hair within about 24 hours after the pre-alkalizing step.

2. The method according to claim 1, wherein the pre-alkalizing composition contains at least one auxiliary ingredient chosen from rheology-modifying agents, chelants, fatty substances, surfactants, substantive polymers, ceramides, alkoxyaminosilicones, fragrances, and silanes.

3. The method according to claim 1, wherein the color-altering composition is a ready-to-use composition.

4. The method according to claim 1, wherein the at least one direct dye is chosen from azo direct dyes, methine direct dyes, carbonyl direct dyes, azine direct dyes, nitro (hetero) aryl direct dyes, tri (hetero) arylmethane direct dyes, addition salts thereof, and mixtures thereof.

5. The method according to claim 1, wherein the at least one direct dye is present in an amount ranging from about 0.001% to about 20% by weight, relative to the total weight of the color-altering composition.

6. The method according to claim 1, wherein the at least one oxidative dye precursor is chosen from ortho aminophenols, para aminophenols, ortho phenylenediamines, para phenylenediamines, double bases, heterocyclic bases, acid addition salts thereof, and mixtures thereof.

7. The method according to claim 1, wherein the color-altering composition further comprises at least one auxiliary ingredient chosen from rheology-modifying agents, activators, chelants, fatty substances, ceramides, alkoxyaminosilicones, silanes, and lift-enhancing agents chosen from nitrogen-containing compounds and metal catalyst compounds.

8. The method according to claim 1, wherein the color-altering composition further comprises at least one fatty substance.

9. The method according to claim 1, wherein the color-altering composition is applied onto the hair within a time period of less than 12 hours after the pre-alkalizing composition is applied onto the hair.

10. The method according to claim 1, wherein the color-altering composition is left on the hair for a time period ranging from about 3 to about 60 minutes.

11. The method according to claim 1, further comprising applying a post-treatment composition onto the hair.

12. The method according to claim 11, wherein the post-treatment composition contains at least one auxiliary ingredient chosen from rheology-modifying agents, chelants, fatty substances, ceramides, alkoxyaminosilicones, and silanes.

13. The method according to claim 1, further comprising applying heat to the hair after the application of the color-altering composition onto the hair.

14. A method of altering the appearance of hair, said method comprising:
   (a) applying, onto the hair, a pre-alkalizing composition having a pH of from about 8 to about 14, wherein the pre-alkalizing composition changes the shape of the hair, and wherein the pre-alkalizing composition is left on the hair for a time period sufficient to form pre-alkalized hair having an alkaline pH;
   (b) optionally, rinsing the hair;

(c) shampooing the hair and rinsing the shampooed hair;
(d) applying a color-altering composition onto the pre-alkalized hair, wherein the color-altering composition comprises, in a cosmetically acceptable carrier:
 (i) at least one direct dye;
 (ii) at least one additional ingredient chosen from rheology-modifying agents, activators, chelants, fatty substances, lift-enhancing agents, de-dusting agents, alkoxyaminosilicones, silane compounds, and ceramide compounds; and
 (iii) optionally at least one oxidative dye precursor;
  and wherein the pH of the color-altering composition ranges from about 1 to about 7;
(e) leaving the color-altering composition on the hair for a time period sufficient to achieve a desired level of color lift; and
(f) optionally, rinsing the hair;
wherein the color-altering composition does not comprise a chemical oxidizing agent; and
wherein the color-altering composition is applied onto the pre-alkalized hair within about 24 hours after the pre-alkalizing step.

15. The method according to claim 14, wherein the at least one direct dye is present in an amount ranging from about 0.001% to about 20% by weight, relative to the total weight of the color-altering composition.

16. The method according to claim 14, wherein the color-altering composition is applied onto the hair within a time period of less than 12 hours after the pre-alkalizing composition is applied onto the hair.

17. The method according to claim 14, wherein the color-altering composition is left on the hair for a time period ranging from about 3 to about 60 minutes.

18. The method according to claim 14, further comprising applying a post-treatment composition onto the hair.

19. The method according to claim 18, wherein the post-treatment composition contains at least one auxiliary ingredient chosen from rheology-modifying agents, chelants, fatty substances, ceramides, alkoxyaminosilicones, and silanes.

20. The method according to claim 14, further comprising applying heat to the hair after the application of the color-altering composition onto the hair.

* * * * *